(12) United States Patent
Seno et al.

(10) Patent No.: US 6,924,301 B1
(45) Date of Patent: Aug. 2, 2005

(54) COMPOSITION FOR TREATING OR PREVENTING ARRHYTHMIA

(75) Inventors: Kaoru Seno, Osaka (JP); Yozo Hori, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 111 days.

(21) Appl. No.: 10/111,090

(22) PCT Filed: Oct. 16, 2000

(86) PCT No.: PCT/JP00/07153

§ 371 (c)(1),
(2), (4) Date: Apr. 22, 2002

(87) PCT Pub. No.: WO01/30387

PCT Pub. Date: May 3, 2001

(30) Foreign Application Priority Data

Oct. 22, 1999 (JP) .......................................... 11-300296

(51) Int. Cl.$^7$ ...................... A61K 31/42; C07D 413/00; C07F 3/14
(52) U.S. Cl. ........................ 514/376; 514/369; 548/183; 548/226; 548/227; 548/369
(58) Field of Search ............................. 514/369, 376; 548/183, 226, 227, 369

(56) References Cited

U.S. PATENT DOCUMENTS

| | | | | |
|---|---|---|---|---|
| 5,208,244 A | | 5/1993 | Weiss et al. ................ | 514/336 |
| 5,434,288 A | | 7/1995 | Lennon et al. .............. | 558/182 |
| 5,955,616 A | * | 9/1999 | Ohtani et al. ............... | 548/183 |
| 6,147,100 A | * | 11/2000 | Seno et al. .................. | 514/369 |

FOREIGN PATENT DOCUMENTS

| | | |
|---|---|---|
| EP | 0 544 488 A2 | 6/1993 |
| EP | 0 848 004 A1 | 6/1998 |
| EP | 0 976 748 A1 | 2/2000 |
| JP | 9-110835 A2 | 4/1997 |
| JP | 09-110835 | 4/1997 |
| JP | 09-268153 | 10/1997 |
| WO | WO 97/05135 A1 | 2/1997 |
| WO | WO 98/08818 A1 | 3/1998 |
| WO | WO 98/33797 A1 | 8/1998 |

OTHER PUBLICATIONS

Dewindt, et al., "Phospholipase $A_2$–mediated hydrolysis of cardiac phospholipids: The use of molecular and transgenic techniques", *Molecular and Cellular Biochemistry*, 180: 65–73, (1998), Kluwer Academic Publishers, The Netherlands.

Fazekas, et al., "Effect of Chloroquine in Experimental Myocardial Ischaemia", *Acta Physiologica Hungarica*, pp. 191–199, vol. 72 (2), (1988), Akadémiai Kiadó, Budapest.

Filippov, et al., "$Ca^{2+}$–Antagonistic Properties of Phospholipase $A_2$ Inhibitors, Mepacrine and Chloroquine", *Gen. Physiol. Biophys.*, 8, 113–118 (1989), 14292 Poshchino, Moscow Region, USSR.

Shaikh, et al., "Amiodarone—an inhibitor of phospholipase activity: a comparative study of the inhibitory effects of amiodarone, chloroquine and chlorpromazine", *Molecular and Cellular Biochemistry* 76: 163–172 (1987), Martinus Nijhoff Publishers, Boston—Printed in The Netherlands.

Dole et al., "Microdetermination of Long–chain Fatty Acids in Plasma and Tissues," *The Journal of Biological Chemistry*, Sep. 1990, pp. 2595–2599, vol. 235, No. 9.

Kramer et al., "The $Ca^{2+}$–sensitive Cytosolic Phospholipase $A_2$ Is a 100–kDa Protein in Human Monoblast U937 Cells," *The Journal of Biological Chemistry*, Mar. 15, 1991, pp. 5268–5272, vol. 266, No. 8.

Manning et al., "Ischemia and Reperfusion–Induced Arrhythmaias in the Rat," *Circulation Research*, Oct. 1984, pp. 545–548, vol. 55, No. 4.

Sedlis et al., "Time course of lysophosphatidylcholine release from ischemic human myocardium parallels the time course of early ischemic ventricular arrhythmia," *Coronary Artery Disease*, Jan. 1997, pp. 19–27, vol. 8, No. 1.

Murakami et al., "Functional Coupling Between Various Phospholipase $A_2$s and Cyclooxygenases in Immediate and Delayed Prostanoid Biosynthetic Pathways," *The Journal of Biological Chemistry*, Jan. 29, 1999, pp. 3103–3115, vol. 274, No. 5.

* cited by examiner

Primary Examiner—Dwayne Jones
(74) Attorney, Agent, or Firm—Foley & Lardner LLP

(57) ABSTRACT

A composition for treating or preventing arrhythmia containing as an active ingredient a $cPLA_2$ inhibitor, for example a compound represented by formula (I):

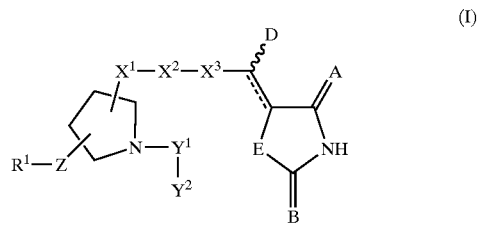

wherein $R^1$ is optionally substituted aralkyl or the like; Z is —S— or the like; $X^1$ is —$(CH_2)$s-$N(R^{18})$—CO— (wherein $R^{18}$ is hydrogen atom or the like, s is an integer of 0 to 3) or the like; $X^2$ is optionally substituted arylene or the like; $X^3$ is a bond or the like; A, B, and E are each independently oxygen atom or sulfur atom; D is hydrogen atom or the like; $Y^1$ is —$(CH_2)mCO$— (m is an integer of 0 to 3) or the like; $Y^2$ is optionally substituted aryl or the like.

6 Claims, No Drawings

US 6,924,301 B1

COMPOSITION FOR TREATING OR PREVENTING ARRHYTHMIA

TECHNICAL FIELD

The present invention relates to compositions for treating or preventing arrhythmia containing as the active ingredients inhibitors of $cPLA_2$ (cytosolic phospholipase $A_2$).

BACKGROUND ART

Arrhythmia is a disease which is caused by dysfunction of ion channel due to abnormality of the channel gene or acquired diseases, by of artificial pathologic condition or by the remodeling of the channel inducing change of structure or expression. As a therapeutic agent of arrhythmia, local anesthetics (e.g., lidocaine and the like), β receptor blockers (e.g., propranolol and the like), and calcium channel blocker (e.g., verapamil or the like) are now used. The other agents include Na channel inhibitors, Ca channel inhibitors, and Na—H exchange inhibitors.

Possibility of lysophospholipid inducing arrhythmia is described in Coron. Artery Dis. 8, 19–27 (1997) without any description about cPLA2 inhibitors.

As cPLA2 inhibitors are disclosed indole derivatives (WO98/08818), benzene derivatives (EP544488, JP Laid-Open No.286852/93), trifluoromethylketone derivatives (JP Laid-Open No.268153/97), azaspiro derivatives (JP Laid-Open No.110835/97), pyrrolidine derivativs (WO97/05135, WO98/33797) and the like. However, there is no concrete description therein about the utility of these compounds for treating or preventing arrhythmia.

DISCLOSURE OF INVENTION

The present invention provides compositions for treating or preventing arrhythmia containing as the active ingredients $cPLA_2$ inhibitors.

The present invention relates to I) a composition for treating or preventing arrhythmia containing as an active ingredient a $cPLA_2$ inhibitor.

Mentioned in more detail, the invention relates to II) to VIII).

II) A composition for treating or preventing arrhythmia containing as an active ingredient a compound represented by formula (I):

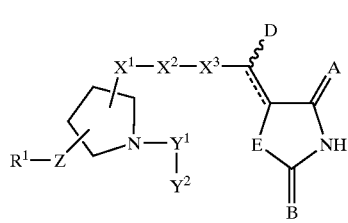

wherein $R^1$ is hydrogen atom, lower alkyl, optionally substituted aryl, aryl fused with a non-aromatic hydrocarbon ring or a non-aromatic heterocyclic ring, optionally substituted aralkyl, optionally substituted arylcarbonyl, or optionally substituted heteroaryl; Z is —S—, —SO—, —O—, —$OCH_2$—, —CONH—, $CONHCH_2$—, —$N(R^{16})$— (wherein $R^{16}$ is hydrogen atom, lower alkyl, $C_3$–$C_8$ cycloalkyl lower alkyl or aralkyl), or a bond;
$X^1$ is —$(CH_2)_q$—CO— (wherein q is an integer of 0 to 3), —$(CH_2)_r$—CO—$N(R^{17})$— (wherein $R^{17}$ is hydrogen atom or lower alkyl, and r is an integer of 0 to 3), —$CH_2NHSO_2$—, —$(CH_2)_s$-$N(R^{18})$—CO— (wherein $R^{18}$ is hydrogen atom or lower alkyl, s is an integer of 0 to 3), —$CH_2NHCOCH_2O$—, —$CH_2N(R^{19})$COCH=CH— (wherein $R^{19}$ is hydrogen atom or lower alkyl), —$CH_2NHCS$—, —$CH_2O$—, —$OCH_2$—, —$CH_2OCH_2$—, —$CH_2$—$N(R^{20})$—$CH_2$— (wherein $R^{20}$ is hydrogen atom, lower alkyl, or acyl), alkylene, alkenylene, or a bond;
$X^2$ is optionally substituted arylene, optionally substituted heteroarylene, heterocycle-diyl, —C≡C—, or a bond;
$X^3$ is alkylene, alkenylene, or a bond;
A, B, and E are each independently oxygen atom or sulfur atom;
D is hydrogen atom or hydroxy lower alkyl;
$Y^1$ is —$(CH_2)$mCO—, —$(CH_2)$mCONH—, —$(CH_2)$mCSNH—, —$(CH_2)$m$SO_2$—, —$(CH_2)$mCOO—, —$(CH_2)$nNHCO—, —$(CH_2)$nNH$SO_2$—, or a bond; m is an integer of 0 to 3; n is an integer of 1 to 3;
$Y^2$ is hydrogen atom, optionally substituted lower alkyl, optionally substituted lower alkenyl, optionally substituted cycloalkyl, optionally substituted lower cycloalkenyl; optionally substituted aryl, optionally substituted aralkyl, optionally substituted heteroaryl, or optionally substituted amino;
a broken line (---) represents the presence or absence of a bond; a wavy line (~) represents cis or trans configuration of D to E, its prodrug, its pharmaceutically acceptable salt, or hydrate thereof.

III) A composition for treating or preventing arrhythmia containing as an active ingredient a compound represented by formula (II):

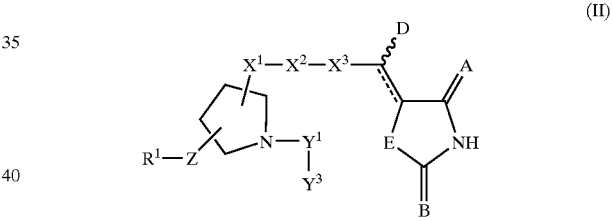

wherein $R^1$, $X^1$, $X^2$, $X^3$, D, $Y^1$, a broken line (---) and a wavy line (~) are as defined above,
$Y^3$ is represented by formula:

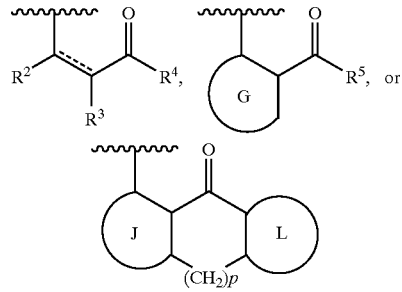

wherein $R^2$ and $R^3$ are both hydrogen atom or one is optionally substituted aryl, optionally substituted heteroaryl, or optionally substituted cycloalkyl, and the other is hydrogen atom or lower alkyl; $R^4$, $R^5$, G ring, J ring, and L ring are each independently optionally substituted aryl, optionally substituted heteroaryl, optionally substituted cycloalkyl, or cycloalkenyl; a broken line (---) represents the presence or absence of a bond;

p is an integer of 0 to 2;

its prodrug, its pharmaceutically acceptable salt, or hydrate thereof.

IV) A composition of III) for treating or preventing arrhythmia containing as an active ingredient a compound represented by formula (III):

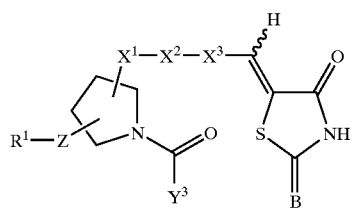

(III)

wherein $R^1$, Z, $X^1$, $X^2$, $X^3$, $Y^3$, B, and a wavy line (~) are as defined above, its prodrug, its pharmaceutically acceptable salt, or hydrate thereof.

V) A composition of III) for treating or preventing arrhythmia containing as an active ingredient a compound represented by formula (IV):

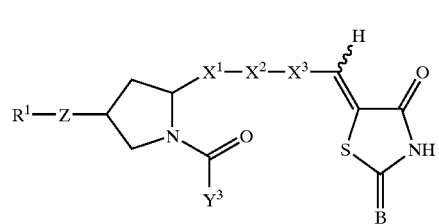

(IV)

wherein $R^1$, Z, $X^1$, $X^2$, $X^3$, $Y^3$, B, and a wavy line (~) are as defined above, its prodrug, its pharmaceutically acceptable salt, or hydrate thereof.

VI) A composition of III) for treating or preventing arrhythmia containing as an active ingredient a compound represented by formula (V):

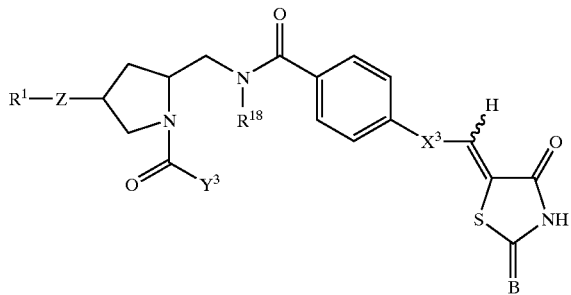

(V)

wherein $R^1$, Z, $R^{18}$, $X^3$, $Y^3$, B, and a wavy line (~) are as defined above, its prodrug, its pharmaceutically acceptable salt, or hydrate thereof.

VII) A composition in any one of III) to VI), for treating or preventing arrhythmia containing as an active ingredient a compound, wherein Z is —S— or —N($R^{16}$)— (wherein $R^{16}$ is as defined above), $X^3$ is a bond, $R^1$ is optionally substituted aralkyl, $Y^3$ is represented by the formula:

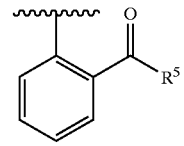

wherein $R^5$ is optionally substituted aryl, its prodrug, its pharmaceutically acceptable salt, or hydrate thereof.

VIII) Composition in any one of I) to VII), for treating or preventing arrhythmia, wherein the arrhythmia occurrs after ischemia reperfusion.

IX) Use of a $cPLA_2$ inhibitor of I) or a compound of any one of II) to VII) for preparation of a pharmaceutical composition for treating arrhythmia.

X) A method for treating arrhythmia of a mammal, including a human, which comprises administration to said mammal of a $cPLA_2$ inhibitor of I) or a compound of any one of II) to VII) in a pharmaceutically effective amount.

The term "halogen" herein used means fluoro, chloro, bromo, and iodo.

The term "lower alkyl" herein used means $C_1$–$C_{10}$ straight or branched chain alkyl. $C_1$–$C_6$ straight or branched chain alkyl are preferred as the lower alkyl. Examples of the lower alkyl include methyl, ethyl, n-propyl, isopropyl, n-butyl, isobutyl, sec-butyl, tert-butyl, n-pentyl, isopentyl, n-hexyl, n-heptyl, n-octyl n-nonyl, n-decyl, (2,6-dimethylheptan)-4-yl and the like.

Methyl, ethyl, n-propyl, and isopropyl and (2,6-dimethylheptan)-4-yl are preferred as the lower alkyl for $R^1$, $R^2$, $R^3$, $R^{17}$, $R^{18}$, $R^{19}$, and $R^{20}$. Particularly, methyl is preferred.

Examples of the lower alkyl for $R^{16}$ are methyl, ethyl, isopropyl, isobutyl, and isopentyl. Isopropyl, isobutyl, and isopentyl are preferred.

The term of "$C_3$ to $C_8$ cycloalkyl lower alkyl" for $R^{16}$ means above-mentioned "lower alkyl" substituted with $C_3$ to $C_8$ cycloalkyl (e.g., cyclopropyl, cyclopentyl, cyclobutyl, cyclohexyl, cycloheptyl and cyclooctyl). Examples of it are cyclopropylmethyl, cyclobutylmethyl, cyclopentylmethyl, and cyclohexylmethyl.

The term "cycloalkyl" herein used means $C_3$–$C_7$ cycloalkyl. Examples of the cycloalkyl are cyclopropyl, cyclobutyl, cyclopentyl, cyclohexyl, and cycloheptyl. Cyclopentyl, cyclohexyl, and cycloheptyl are preferred. Particularly, cyclopentyl and cyclohexyl are preferred.

The term "cycloalkenyl" herein used means $C_3$–$C_7$ cycloalkenyl having one or more unsaturated bond(s) in the ring. Examples of the cycloalkenyl are cyclopropenyl, cyclopentadienyl, cyclohexenyl, and the like. Cyclohexenyl is preferred.

The term "a non-aromatic heterocyclic ring" herein used means a 5 to 7 membered non-aromatic ring which contains one or more hetero atoms selected from the group consisting of oxygen, sulfur and nitrogen atoms in the ring or a fused ring comprising of two or more of such rings. Examples of the non-aromatic heterocyclic ring are pyrrolidine, piperidine, piperazine, octahydroquinoline, tetrahydrofuran, tetrahydropyrane, and the like.

The term "aryl" herein used means a monocyclic or fused aromatic hydrocarbon ring or a group containing continuously bonded two or more of the monocyclic aromatic hydrocarbon rings. Examples of the aryl are phenyl, 1-naphthyl, 2-naphthyl, biphenylyl, indenyl, 2-p-terphenyl, 2-m-terphenyl, 2-o-terphenyl, anthryl, phenathryl, and the like. Phenyl, 1-naphthyl, 2-naphthyl, anthryl, phenanthryl, 2-biphenylyl, 3-biphenylyl, 4-biphenylyl, 2-p-terphenyl, 2-m-terphenyl, 2-o-terphenyl are preferred.

The term "aryl fused with a non-aromatic hydrocarbon ring" herein used means phenyl, 1-naphthyl, and 2-naphthyl which are fused with the above-mentioned "cycloalkyl". Examples of it are indanyl, 1,2,3,4-tetrahydronaphthyl, acenaphtyl, and the like. Indanyl and 1,2,3,4-tetrahydronaphthyl are preferred.

The term "aryl fused with a non-aromatic heterocyclic ring" herein used means phenyl, 1-naphthyl, and 2-naphthyl which are fused with the above-mentioned "a non-aromatic heterocyclic ring". Examples of it are indolyl, isoindolyl, 2,3,6,7-tetrohydro-1H,5H-pyrido[3,2,1-ij]quinolyl, isochromanyl, chromanyl, and the like. 2,3,6,7-tetrohydro-1H,5H-pyrido[3,2,1-ij]quinolyl is preferred.

The term "aralkyl" herein used means the above-mentioned "lower alkyl" substituted with the above-mentioned "aryl". Examples of the aralkyl are benzyl, phenethyl, 3-phenyl-n-propyl; benzhydryl, naphthylmethyl, naphthylethyl, and the like. Benzyl, benzhydryl, phenethyl, and naphthylmethyl are preferred. Particularly, benzyl and benzhydryl are preferred.

The term "alkylene" herein used means a group derived from $C_1$–$C_5$ alkyl. Examples of the alkylene are methylene, ethylene, trimethylene, tetramethylene, and pentamethylene.

The term "alkenylene" herein used means a group derived from $C_2$–$C_4$ alkenyl. Examples of the alkenylene are vinylene, propenylene, and butenylene.

The term "arylene" herein used means a group derived from the above-mentioned "aryl". Examples of the arylene are phenylene, naphthylene, and the like. Mentioned in more detail, it is exemplified by 1,2-phenylene, 1,3-phenylene, 1,4-phenylene, and the like.

The term "heteroarylene" herein used means a group derived from the "heteroaryl" mentioned below. Examples of the heteroarylene are thiophendiyl, furandiyl, and the like. Mentioned in more detail, it is exemplified by 2,5-thiophendiyl, 2,6-furandiyl, and the like.

The term "heterocycle-diyl" herein used means a group derived from the above-mentioned "a non-aromatic heterocyclic ring". Examples of the heterocycle-diyl are pyrrolidinediyl, piperidinediyl, piperazinediyl, and the like. Mentioned in more detail, it is exemplified by 1,4-piperidinediyl and the like.

The term "hydroxy lower alkyl" herein used means the above-mentioned "lower alkyl" substituted with hydroxy. Examples of the hydroxy lower alkyl are hydroxymethyl, 1-hydroxyethyl, 2-hydroxyethyl and the like.

The term "heteroaryl" herein used means a 5 to 6 membered aromatic mono heterocyclic group which contains one or more hetero atoms selected from the group consisting of nitrogen, oxygen and sulfur atoms in the ring or the heterocyclic group fused with phenyl. Examples of the heteroaryl are pyrrole, pyrrolyl, pyridyl, thienyl, furyl, benzofuryl, benzothienyl, indolyl, and the like. Pyridyl, thienyl, furyl, benzo[b]thienyl, benzo[b]furanyl, and indolyl are preferred.

The term "lower alkyloxy" herein used means alkyloxy of which alkyl part is the above-mentioned "lower alkyl". Examples of the alkyloxy are methyloxy, ethyloxy, n-propyloxy, isopropyloxy, n-butyloxy, isobutyloxy, sec-butyloxy, t-butyloxy, and the like. Methyloxy, ethyloxy, and n-propyloxy are preferred.

The term "optionally substituted aryl" herein used for $R^1$ means the above mentioned "aryl" which may be substituted with one or more substituents selected from the group consisting of phenyl $C_2$–$C_4$ alkenyl (e.g., phenylethenyl), lower alkyl (e.g., methyl, ethyl, isopropyl, isobutyl, and t-butyl), cycloalkyl (e.g., cyclopentanyl and cyclohexenyl), halogen (e.g., fluoro, chloro, bromo, and iodo), lower alkyloxy (e.g., methyloxy and ethyloxy), trihalo lower alkyl (e.g., trifluoromethyl and trichloromethyl), nitro, phenyl, naphthyl (e.g., 1-naphthyl and 2-naphthyl), phenanthryl (e.g., 9-phenanthryl), benzo-1,3-dioxolanyl (e.g., 4-benzo-1,3,-dioxolanyl and 5-benzo-1,3-dioxolanyl), heteroaryl (e.g., 3-pyridyl, 3-thienyl, and 2-benzothienyl), aralkyl (e.g., benzyl and phenethyl), aryloxy (e.g., phenyloxy), hydroxy, amino, mono- or di-substituted amino (e.g., dimethylamino, diethylamino, phenylamino, N-methyl-N-phenylamino, and N-methyl-N-benzylamino), piperazinyl which may be substituted with the above mentioned lower alkyl (e.g., 4-methylpiperazinyl), and the like. Examples of optionally substituted aryl for $R^1$ are phenyl, 2-biphenylyl, 3-biphenylyl, 4-biphenylyl, 1-naphthyl, 2-naphthyl, 2-p-terphenyl, 2-m-terphenyl, 2-o-terphenyl, 2-isopropylphenyl, 2-t-butylphenyl, 2-isobutylphenyl, 2-cyclopentylphenyl, 2-bromophenyl, 3-bromophenyl, 2-iodophenyl, 2-(4-benzo-1,3-dioxolanyl)phenyl, 2-(5-benzo-1,3-dioxolanyl)phenyl, 2-phenoxyphenyl, 2-benzylphenyl, 2-(3-pyridyl)phenyl, 3-dimethylaminophenyl, 3-diethylaminophenyl, 3-phenylaminophenyl, 3-(N-methyl-N-phenylamino)phenyl, 2-(1-naphthyl)phenyl, 2-(2-naphthyl)phenyl, 3-(1-naphthyl)phenyl, 3-(2-naphthyl)phenyl, 4-(ethenylphenyl)phenyl, 2-bromo-6-isopropylphenyl, 2-isopropyl-6-phenyl-phenyl, 2-isopropyl-6-(1-naphthyl)phenyl, 2-bromo-6-nitrophenyl, 2-methyloxy-6-(1-naphthyl)phenyl, 2'-methyl-2-biphenyl, 2'-isopropyl-2-biphenyl, 2'-methyloxy-2-biphenyl, 3'-methyl-2-biphenyl, 3'-trifluoromethyl-2-biphenyl, 3'-nitoro-2-biphenyl, 3'-methyloxy-2-biphenyl, 3'-ethyloxy-2-biphenyl, 3'-hydroxy-2-biphenyl, 3-methyloxy-2-biphenyl, 6-phenyl-2-naphthyl, 1-bromo-6-phenyl-2-naphthyl, 1,6-diphenyl-2-naphthyl, 4-phenyl-1-naphthyl, 2-(4-methylpiperazinyl)phenyl, and the like.

The term "optionally substituted aryl" herein used for $R^2$, $R^3$, $R^4$, $R^5$, G ring, J ring, and L ring means the above mentioned "aryl" which may be substituted with one or more substituents selected from the group consisting of halogen (e.g., fluoro, chloro, bromo, and iodo), lower alkyl (e.g., methyl, ethyl, n-propyl, and isopropyl), lower alkyloxy (e.g., methyloxy and ethyloxy), trihaloalkyl (e.g., trifluoromethyl), alkyloxycarbonyl (e.g., mehtyloxycarbonyl), acyl (e.g., acetyl), amino, mono- or di-substituted amino (e.g., acylamino and methylamino), and the like, The term "optionally substituted aryl" herein used for $Y^2$ means the above mentioned "aryl" which may be substituted with one or more substituents selected from the group consisting of halogen (e.g., fluoro, chloro, bromo, and iodo), lower alkyl (e.g., methyl, ethyl, n-propyl, and isopropyl), lower alkyloxy (e.g., methyloxy and ethyloxy), trihaloalkyl (e.g., trifluoromethyl), alkyloxycarbonyl (e.g., methyloxycarbonyl), acyl (e.g., acetyl), amino, mono- or di-substituted amino (e.g., acylamino and methylamino), and the like, or means above-mentioned "aryl" which may be substituted with —$COR^5$ (wherein $R^5$ is as defined above). Furthermore, the aryl may be condensed with non-aromatic hydrocarbon ring condensed with aryl or may be condensed with non-aromatic hydrocarbon ring condensed with heteroaryl.

The term "optionally substituted aralkyl" herein used for $R^1$ means the above mentioned "lower alkyl" substituted with one or more of the above-mentioned "optionally substituted aryl" for $R^1$ or the above-mentioned "optionally substituted heteroaryl" for $R^1$. Examples of the optionally substituted aralkyl for $R^1$ are benzyl, phenethyl, 2-biphenylmethyl, 3-biphenylmethyl, 4-biphenylmethyl, 1-naphthylmethyl, 2-naphthylmethyl, 2-p-terphenylmethyl, 2-m-terphenylmethyl, 2-o-terphenylmethyl, diphenylmethyl, 2-isopropylphenyl, 2-t-butylphenylmethyl, 2-isobutylphenylmethyl, 2-cyclopentylphenylmethyl, 2-bromophenylmethyl, 3-bromophenylmethyl, 2-iodophenylmethyl, 2-(4-benzo-1,3-dioxolanyl) phenylmethyl, 2-(5-benzo-1,3-dioxolanyl)phenylmethyl, 2-phenoxyphenylmethyl, 2-benzylphenylmethyl, 2-phenethylmethyl, 2-(3-thienyl)phenylmethyl, 2-(2-benzothienyl)phenylmethyl, 2-(3-pyridyl)phenylmethyl, 3-dimethylaminophenylmethyl, 3-diethylaminophenylmethyl, 3-phenylaminophenylmethyl, 3-(N-methyl-N-phenylamino)phenylmethyl, 2-(1-naphthyl)phenylmethyl, 2-(2-naphthyl)phenylmethyl, 3-(1-naphthyl)phenylmethyl, 3-(2-naphthyl)phenylmethyl, 2-(9-phenanthryl)phenylmethyl, 4-(ethenylphenyl)phenylmethyl, 2-bromo-6-isopropylphenylmethyl, 2-isopropyl-6-phenyl-phenylmethyl, 2-isopropyl-6-(1-naphthyl)phenylmethyl, 2-bromo-6-nitrophenylmethyl, 2-methyloxy-6-(1-naphthyl)phenylmethyl, 2'-methyl-2-biphenylmethyl, 2'-isopropyl-2-biphenylmethyl, 2'-methyloxy-2-biphenylmethyl, 3'-methyl-2-biphenylmethyl, 4'-fluoro-2-biphenylmethyl, 3'-trifluoromethyl-2-biphenylmethyl, 3'-nitro-2-biphenylmethyl, 3'-methyloxy-2-biphenylmethyl, 3'-ethyloxy-2-biphenylmethyl, 3'-hydroxy-2-biphenylmethyl, 3-methyloxy-2-biphenylmethyl, 6-phenyl-2-naphthylmethyl, 1-bromo-6-phenyl-2-naphthylmethyl, 1,6-diphenyl-2-naphthylmethyl, 4-phenyl-1-naphthylmethyl, 1-phenyl-2-naphthylmethyl, 1-phenylphenylmethyl, 2-phenylphenylmethyl, 2,6-diphenylmethyl, 1,1-di(4-methyloxyphenyl)-phenylmethyl, 1,1-di(3-fluorophenyl)phenylmethyl, 1,1-diphenyl(3,5-difluorophenyl)methyl, 1,1-diphenyl(3,5-dimethylphenyl)methyl, 1,1-di(3-methylphenyl)phenylmethyl, tosyl, 1,1-diphenyl(4-methyloxyphenyl)methyl, 1,1-diphenyl(4-methylphenyl)methyl, 1,1,1-tri(4-fluorophenyl)methyl, 1,1-diphenyl(2-methylphenyl)methyl, 1,1-diphenyl(3-methylphenyl)methyl, 1,1,1-tri(4-chlorophenyl)methyl, 1,1-diphenyl(3-isopropylphenyl)methyl, 1,1-diphenyl(2-thienyl)methyl, 1,1-diphenyl(2-fluorophenyl)methyl, 1,1-diphenyl(3-fluorophenyl)methyl, 1,1-diphenyl(4-fluorophenyl)methyl, and the like.

The term "optionally substituted heteroaryl" herein used for $R^1$ means the above-mentioned "heteroaryl" which may be substituted with one or more substituents as exemplified for the above-mentioned "optionally substituted aryl" for $R^1$.

The term "optionally substituted heteroaryl" herein used for $Y^2$ means the above mentioned "heteroaryl" which may be substituted with one or more substituents selected from the group consisting of halogen (e.g., fluoro, chloro, bromo, and iodo), lower alkyl (e.g., methyl, ethyl, n-propyl, and isopropyl), lower alkyloxy (e.g., methyloxy and ethyloxy), trihaloalkyl (e.g., trifluoromethyl), alkyloxycarbonyl (e.g., methyloxycarbonyl), acyl (e.g., acetyl), amino, mono- or di-substituted amino (e.g., acylamino and methylamino), and the like, or means above-mentioned "heteroaryl" which may be substituted with —$COR^6$ (wherein $R^5$ is as defined above). Furthermore, the heteroaryl may be condensed with non-aromatic hydrocarbon ring condensed with aryl or may be condensed with non-aromatic hydrocarbon ring condensed with heteroaryl.

The term "optionally substituted heteroaryl" herein used for $R^2$, $R^3$, $R^4$, $R^5$, G ring, J ring, and L ring means the above mentioned "heteroaryl" in which any of the carbon atoms in the ring may be substituted with one or more substituents selected from the group consisting of halogen (e.g., fluoro, chloro, bromo, and iodo), lower alkyl (e.g., methyl and ethyl), lower alkyloxy (e.g., methyloxy and ethyloxy), alkyloxycarbonyl (e.g., methyloxycarbonyl), and the like. When the hetero atom is nitrogen, the nitrogen atom is optionally substituted with optionally substituted lower alkyl, acyl, and the like.

The term of the arylene of "optionally substituted arylene" herein used means the above mentioned "arylene", and the substituents mean substituents as exemplified for the above-mentioned "optionally substituted aryl" for $R^2$, $R^3$, $R^4$, $R^5$, G ring, J ring, and L ring. Examples of the optionally substituted arylene are 1,4-phenylene, 2-hydroxy-1,4-phenylene, and the like. 1,4-phenylene is preferred.

The substituents of "optionally substituted heteroarylene" herein used means substituents as exemplified for the above-mentioned "optionally substituted aryl" for $R^2$, $R^3$, $R^4$, $R^5$, G ring, J ring, and L ring. Examples of the optionally substituted arylene are 2,5-thiophendiyl, 2,5-furandiyl, 2,5-pyridinediyl and the like. 2,5-thiophendiyl is preferred.

The term "optionally substituted arylcarbonyl" herein used means carbonyl which may be substituted with the above mentioned "optionally substituted aryl".

The substituents of "optionally substituted lower alkyl", "optionally substituted cycloalkyl", and "optionally substituted cycloalkenyl" are exemplified by lower alkyloxy, lower alkyloxycarbonyl, carboxy, monoalkyl-substituted amino, dialkyl-substituted amino, and the like.

The term "optionally substituted lower alkyloxy" herein used means the above-mentioned "lower alkyloxy" which may be substituted with the substituents as exemplified for the above-mentioned "optionally substituted alkyl". Examples of the optionally substituted lower alkyloxy are methyloxycarbonylmethyloxy, methyloxycarbonylethyloxy, ethyloxycacrbonylmethyloxy, ethtyloxycarbonylethyloxy, dimethylaminomethyloxy, dimethylaminoehtyloxy, and the like.

The term "acyl" herein used means alkylcarbonyl of which alkyl part is the above mentioned "lower alkyl" and arylcarbonyl of which aryl part is the above mentioned "aryl". Furthermore, the aryl part of "arylcarbonyl" is optionally substituted with lower alkyl, halogen, and the like.

Examples of the acyl are acetyl, propionyl, benzoyl, toluoyl, and the like.

In the present specification, the term "optionally substituted amino" means amino substituted with one or two of the above mentioned "lower alkyl", the above mentioned "aralkyl", or the above mentioned "acyl". Examples of the optionally substituted amino are methylamino, ethylamino, n-propylamino, dimethylamino, diethylamino, ethylmethylamino, benzylamino, acetylamino, benzoylamino and the like.

BEST MODE FOR CARRYING OUT THE INVENTION

Pyrrolidine derivatives which are used in a composition for treating or preventing arrhythmia are able to be synthesized in accordance with the procedure described WO97/05135 and WO98/33797.

The term "solvate" includes, for example, solvates with organic solvents, hydrates, and the like. These hydrates can coordinate with any water molecules.

The term "compound of the present invention" herein used includes a pharmaceutically acceptable salt or solvate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, mallein acid, fumaric acid, benzenesulfonic acid, p-toluenesulfonic acid, and the like). These salts can be formed by the usual method.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example Design of Prodrugs, Elsevier, Amsterdam, (1985). For instance, prodrugs such as an ester derivative which is prepared by reacting a basal acid compound with a suitable alcohol, or an amide derivative which is prepared by reacting a basal acid compound with a suitable amine are exemplified when the compounds according to present invention have a carboxylic group. Particularly preferred esters as prodrugs are methyl, ethyl, n-propyl, isopropyl, n-butyl, isobutyl, tert-butyl, morpholinoethyl, and N,N-diethylglycolamido, and the like. For instance, prodrugs such as an acyloxy derivative which is prepared by reacting a basal hydroxy compound with a suitable acyl halide or a suitable acid anhydride, or when the compounds according to present invention have a hydroxy group. Particularly preferred acyloxy derivatives as prodrugs —$OCOC_2H_5$, —$OCO(t\text{-}Bu)$, —$OCOC_{15}H_{31}$, —$OCO(m\text{-}COONa\text{-}Ph)$, —$OCOCH_2CH_2COONa$, —$OCOCH(NH_2)CH_3$, —$OCOCH_2N(CH_3)_2$, and the like. For instance, prodrugs such as an amide derivative which is prepared by reacting a basal amino compound with a suitable acid halide or a suitable mixed acid anhydride are exemplified when the compounds according to present invention have an amino group. Particularly preferred amide as prodrugs are —$NHCO(CH_2)_{20}CH_3$, —$NHCOCH(NH_2)CH_3$, and the like.

The compound of the present invention is not restricted to any particular isomers but includes all possible isomers and racemic modifications.

When the compound of the present invention is administered to a person for the treatment or prevention of the diseases related to arrhythmia, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 1 to 100 mg/kg/day, and preferably 10 to 50 mg/kg/day and in the case of parenteral administration, the dosage can generally be between 0.1 to 10 mg/kg/day, and preferably 1 to 5 mg/kg/day, which may be administrated in one to several divisions though doctors diagnose finally.

The utility of the present invention for treating or preventing arrhythmia was confirmed in a manner similar to that described in Circulation Research 56: 545–548, 1984.

Wistar male rats are used as experimental animals. Anesthesia of animal is induced by administration of 30 mg/kg to 60 mg/kg, preferably 40 mg/kg of pentobarbital sodium (preferably intraperitoneal injection). A catheter for the administration of drugs is placed in the jugular vein. Electrocardiogram (ECG) is recorded from lead II during cardiac ischemia and reperfusion. A thoracotomy is performed under artificial ventilation. Left coronary artery is ligated with silicon tube for 3 to 5 min, preferably 3 min. Reperfusion is performed by cutting snare. Total duration of ventricular tachycardia and ventricular fibrillation during 5 to 30 min, preferably 10 min reperfusion are evaluated. Test compounds are dissolved in solvent containing 10% DMSO, 10% ethanol, 30% polyethylene glycol and 50% distilled water and sodium hydrocarbonate is added to the solution to adjust final concentration to 0 to 1%, preferably 0.5%. Drugs are administrated intravenously in bolus at 15 to 60 min, preferably 30 min before reperfusion followed by 30 to 40 min, preferably 40 min infusion.

The following examples are provided to further illustrate the present invention and are not to be construed as limiting the scope thereof.

Abbreviations described below are used in the following examples.

Me: methyl
i-Bu: isobutyl
Boc t-butyloxycarbonyl
Tr: trityl
Ms mesyl
DMF: dimethylformamide
THF: tetrahydrofuran
DMSO dimethylsulfoxide
HMPA: hexamethylphosphoramide

EXAMPLE

Example 1

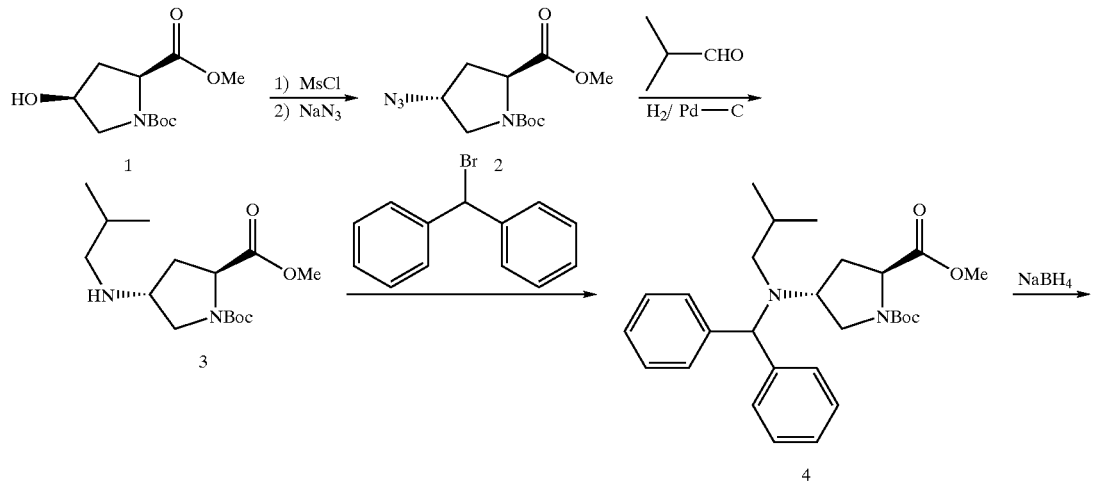

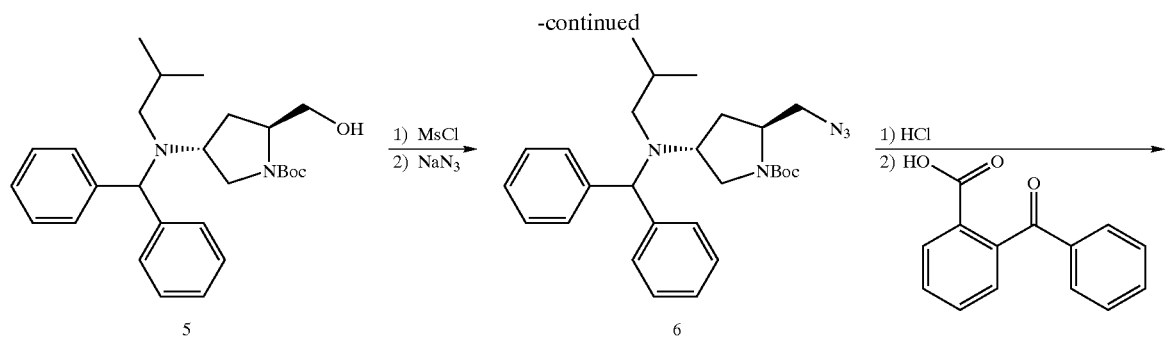

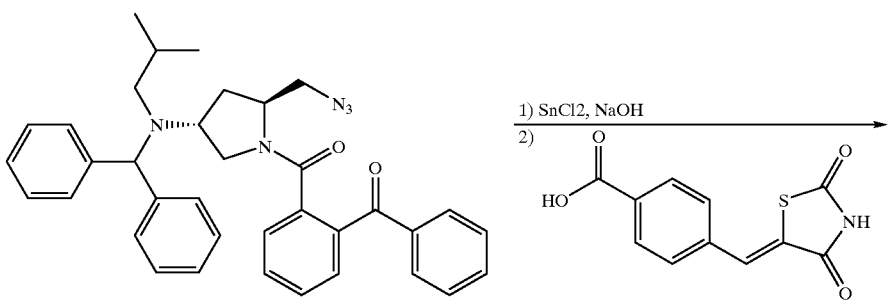

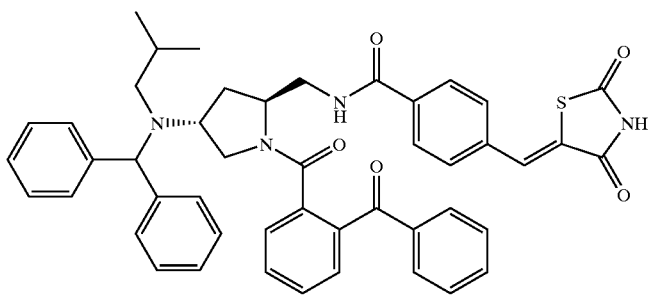

(1) 1→2

To a solution of N-Boc-cis-4-hydroxy-L-proline methyl ester (1) (70.0 g, 285.5 mmol) in THF (600 ml) were added methanesulfonyl chloride (24.3 ml, 314.1 mmol) and triethylamine (43.8 ml, 314.1 mmol) in an ice bath under stirring and the solution was stirred at the same temperature for 0.5 h. To the reaction mixture was added ethyl acetate (500 ml), the organic layer was washed with water, brine successively, dried over sodium sulfate, and evaporated under reduced pressure. To a solution of mesylate as the residue in HMPA (300 ml) was added sodium azide (37.1 g, 571 mmol), and the mixture was stirred at 60° C. for 2 h. The reaction mixture was diluted with ethyl acetate (1000 ml), and the organic layer was washed with water (2000 ml) three times and brine. Drying over sodium sulfate and evaporation of the solvent under reduced pressure gave the crude azide (2) (68.4 g).

$^1$H-NMR (CDCl$_3$) δ(ppm): 1.42 (3/5×9H, s), 1.47 (2/5×9H, s), 2.12–2.23 (1H, m), 2.25–2.40 (1H, m), 3.42–3.71 (3H, m), 3.74 (3H, s), 4.15–4.23 (1H, m), 4.33 (3/5×1H, t, J=7.4 Hz), 4.42 (3/5×1H, t, J=7.4 Hz).

(2) 2→3

To a solution of the above-mentioned azide (2) (20.8 g, 76.96 mmol) in ethanol (200 ml) were added isobutylaldehyde (14.0 ml, 153.9 mmol) and 10% Pd—C (about 1 g) and the reaction mixture was stirred for 12 h at room temperature under hydrogen atmosphere. Filtration of catalyst and evaporation of the solvent under the reduced pressure gave the crude amine(3)(23.6 g).

$^1$H-NMR (CDCl$_3$) δ (ppm): 0.90 (6H, d, J=6.3 Hz), 1.41 (2/3×9H, s), 1.46 (1/3×9H, s), 1.60–1.75 (1H, m), 1.80–2.20 (2H, m), 2.39 (2H, d, J=6.6 Hz), 3.12 (1/3×1H, dd, J=6.0, 10.5 Hz), 3.23 (2/3×1H, dd, J=5.1, 10.5 Hz), 3.34–3.45 (1H, m), 3.67–3.78 (1H, m), 3.73 (3H, s), 4.28–4.36 (2/3×1H, m), 4.37–4.45 (1/3×1H; m).

(3) 3→4

To a solution of the above-mentioned crude amine (3) (7.97 g, 26.54 mmol) in DMF (50 ml) were added a solution of bromodiphenylmethane (19.7 g, 79.63 mmol) in DMF (10 ml) and sodium carbonate (8.44 g, 79.63 mmol) and the mixture was stirred at 100° C. for 2.5 day. The reaction mixture was diluted with ethyl acetate, the organic layer was washed with water and dried over sodium sulfate. Evaporation of the solvent under reduced pressure gave the crude compound (4).

¹H-NMR (CDCl₃) δ (ppm): 0.87–0.94 (6H, m), 1.19–1.28 (1H, m), 1.36 (⅔×9H, s), 1.43 (⅓×9H, s), 1.65–1.97 (2H, m), 2.25–2.35 (1H, m), 2.42 (⅔×1H, d, J=6.3 Hz), 2.46 (⅓×1H, d, J=6.3 Hz), 2.93–3.01 (⅓×1H, m), 3.02–3.11 (⅔×1H, m), 3.26–3.35 (⅓×1H, m), 3.44–3.53 (⅔×1H, m), 3.59 (⅔×3H, s), 3.61 (⅓×3H, s), 3.68–3.80 (1H, m), 4.06–4.13 (⅔×1H, m), 4.17–4.23 (⅓×1H, m), 5.04 (1H, s), 7.21–7.41 (10H, m).

(4) 4→5

To a solution of a whole amount of the above-mentioned compound (4) in THF (50 ml) was added gradually lithium borohydride (1.16 g, 53.08 mmol) in an ice bath. The reaction mixture was stirred in an ice bath for 10 min, and further at room temperature for 1 h. It was cooled in an ice bath and to the mixture were added 2N hydrochloric acid (30 ml) and ice-water to decompose the excess of lithium borohydride carefully. The reaction mixture was diluted with ethyl acetate, the organic layer was washed with water and dried over sodium sulfate. Evaporation of the solvent under reduced pressure gave the oily residue and the purification of it with silica gel column chromatography (chloroform) obtained the alcohol (5) (5.30 g).

¹H-NMR (CDCl₃) δ (ppm): 0.90 (6H, d, J=6.7 Hz), 1.00–1.15 (1H, m), 1.43 (9H, s), 1.66–1.81 (2H, m), 2.31 (1H, dd, J=7.5, 13.4 Hz), 2.42 (1H, dd, J=6.7, 13.4 Hz), 2.90–3.23 (2H, m), 3.28–3.45 (2H, m), 3.55–3.78 (1H, m), 3.83–4.05 (2H, m), 5.05 (1H, s), 7.22–7.37 (11H, m).

IR (KBr). $v_{max}$(cm⁻¹): 3433, 3084, 3060, 3025, 1739, 1693, 1670, 1600.

$[\alpha]_D^{23}$ 10.0±0.5° (c, 1.004, CHCl₃)

Elemental analysis (C₂₇H₃₈N₂O₃) Calcd. C, 73.94; H, 8.73; N, 6.39%. Found C, 74.01; H, 8.70; N, 6.37%.

(5) 5→6

According to the similar preparation of azide (2) from alcohol (1), the extracts with ethyl acetate of the crude azide prepared from the above-mentioned alcohol (5)(1.23 g, 2.807 mmol) was purified with silica gel column chromatography (hexane:ethyl acetate=100:3) to give azide (6) (1.201 g, 92.3%).

¹H-NMR (CDCl₃) δ (ppm): 0.90 (6H, d, J=6.7 Hz), 1.18–1.37 (1H, m), 1.43 (9H, s), 1.65–1.83 (2H, m), 2.25–2.36 (1H, m), 2.41 (1H, dd, J=6.5, 13.2 Hz), 2.83–3.40 (4H, m), 3.66–3.91 (2H, m), 5.05 (1H, s), 7.23–7.38 (10H, m).

IR (KBr) $v_{max}$(cm⁻¹): 2101, 1954, 1890, 1812, 1738, 1694, 1600.

Elemental analysis (C₂₇H₃₇N₅O₂.0.1H₂O) Calcd.: C, 69.68; H, 8.06; N, 15.05%. Found: C, 69.83; H, 7.98; N, 14.79%.

(6) 6→7

To a solution of the above-mentioned azide (6)(194.0 mg, 0.418 mmol) in 1,4-dioxane (3 ml) was added 4N hydrogen chloride in 1,4-dioxane solution (3 ml, 12 mmol), then the solution was stirred at room temperature for 30 min and evaporated under reduced pressure. To a solution of the residue in DMF (3 ml) were added 2-benzoyl benzoic acid (104.1 mg, 0.460 mmol), 1-ethyl-3-(3-dimethylaminopropyl)carbodiimde hydrochloride (88.1 mg, 0.460 mmol), 1-hydroxybenzotriazole (62.2 mg, 0.460 mmol), and triethylamine (0.087 ml, 0.627 mmol) and the mixture was stirred at room temperature for 1 h. The reaction mixture was diluted with ethyl acetate, then the organic layer was washed with water and dried over sodium sulfate. After evaporation of the solvent under reduced pressure, the residue was purified with silica gel column chromatography (hexane:ethyl acetate=4:1) to give the amide (7) (165.2 mg, 69.1%).

¹H-NMR (CDCl₃) δ (ppm): 0.80 (3H, d, J=6.5 Hz), 0.91 (3H, d, J=6.5 Hz), 1.46–1.56 (1H, m), 1.64–1.92 (2H, m), 2.33 (2H, dd, J=2.6, 7.0 Hz), 2.77 (1H, dd, J=8.1, 10.7 Hz), 2.88 (1H, dd, J=8.4, 10.7 Hz), 3.20 (1H, dd, J=3.2, 12.2 Hz), 3.33 (1H, dd, J=6.2, 12.2 Hz), 3.75–3.92 (1H, m), 4.18–4.27 (1H, m), 5.00 (1H, s), 7.14–7.39 (11H, m), 7.40–7.61 (6H, m), 7.75 (2H, d, J=7.0 Hz).

IR (KBr) $v_{max}$(cm⁻¹): 2102, 1659, 1639, 1596.

Elemental analysis(C₃₆H₃₇N₅O₂.0.2H₂O) Calcd.: C, 75.16; H, 6.55; N, 12.17%. Found: C, 75.31; H, 6.56; N, 11.96%.

(7) 7→A-1

To a solution of the above-mentioned compound (7) (126.7 mg, 0.222 mmol) in ethanol (2 ml) and chloroform (0.5 ml) was added a solution of tin (II) chloride dihydrate (100.0 mg, 0.443 mmol) in 1N sodium hydroxide (2.6 ml) in an ice bath under stirring, and then the solution was stirred at same temperature for 10 min and at room temperature for 1 h. After filtration of the precipitation, filtrate was diluted with ethyl acetate, then the organic layer was washed with water and dried over sodium sulfate. After evaporation of the solvent under the pressure, a solution of the residue in DMF (3 ml) was carried out amide bond formation with 4-(2,4-dioxothiazolidine-5-ylidenmethyl)benzoic acid (60.8 mg, 0.244 mmol) according to the similar preparation of the above-mentioned amide (7). The residue which was obtained by extraction with ethyl acetate was purified with silica gel column chromatography (chloroform:methanol= 250:1) to give the product (A-1) (37.9 mg, 22.0%).

¹H-NMR (CDCl₃) δ(ppm): 0.83 (3H, d, J=6.7 Hz), 0.93 (3H, d, J=6.7 Hz), 1.60–1.80 (2H, m), 1.97–2.10 (1H, m), 2.31 (2H, d, J=7.3 Hz), 2.63–2.79 (2H, m), 3.45–3.57 (1H, m), 3.63–3.81 (2H, m), 4.46–4.56 (1H, m), 4.97 (1H, s), 6.95–7.09 (5H, m), 7.21–7.40 (8H, m), 7.41–7.51 (3H, m), 7.53–7.63 (3H, m), 7.69–7.75 (2H, m), 7.71 (1H, s), 7.81 (2H, d, J=7.8 Hz), 8.08 (1H, t, J=5.1 Hz), 8.95 (1H, br. s).

IR (KBr) $v_{max}$(cm⁻¹): 3409, 3058, 3026, 1750, 1709, 1657, 1619, 1538.

Elemental analysis (C₄₇H₄₄N₄O₅S.0.6H₂O) Calcd.: C, 71.66; H, 5.78; N, 7.11; S, 4.07%. Found: C, 71.69; H, 5.68; N, 7.18; S, 4.26%.

The compounds (A-2) to (A-17) were synthesized in a similar manner. Their results were shown in Tables 1 to 3.

TABLE 1

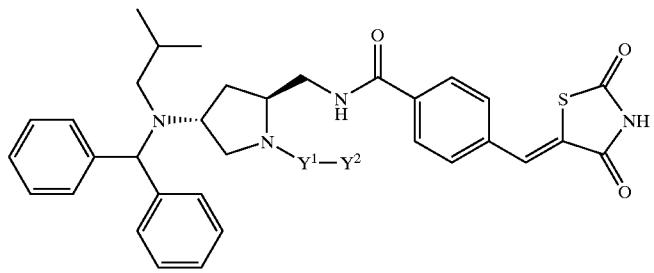

| Compound No. | —Y¹—Y² | NMR (CDCl₃) δ ppm |
|---|---|---|
| A-2 | (2-acetyl-phenyl)(2-fluorophenyl)methanone group | 0.81(1H, d, J=6.5 Hz), 0.91(1H, d, J=6.5 Hz), 1.60–1.80 (2H, m) 1.94–2.1(1H, m), 2.29(2H, d, J=7.2 Hz), 2.61(2H, d, J=7.5 Hz), 3.54–3.85(3H, m), 4.45–4.57(1H, m), 4.94(1H, s), 6.90–7.06(5H, m), 7.11–7.41(10H, m), 7.42–7.66(5H, m), 7.73(1H, s), 7.86(2H, d, J=8.7 Hz), 8.18(1H, t, J=5.1 Hz), 8.60–9.90(1H, br). |
| A-3 | (2-acetyl-phenyl)(3-fluorophenyl)methanone group | 0.83(1H, d, J=6.6 Hz), 0.93(1H, d, J=6.6 Hz), 1.58–1.82 (2H, m), 1.96–2.14(1H, m), 2.32(2H, d, J=7.2 Hz), 2.60–2.80 (2H, m), 3.45–3.90(3H, m), 4.48–4.61(1H, m), 4.98(1H, s), 6.96–7.16(5H, m), 7.20–7.66(15H, m), 7.68(1H, s), 7.80(2H, d, J=8.1 Hz), 8.03(1H, t, J=5.1 Hz) 9.25–9.60(1H, br). |
| A-4 | (2-acetyl-phenyl)(3,5-difluorophenyl)methanone group | 0.84(1H, d, J=6.6 Hz), 0.94(1H, d, J=6.6 Hz), 1.60–1.86 (2H, m), 1.96–2.14(1H, m), 2.33(2H, d, J=7.2 Hz), 2.57–2.84 (2H, m), 3.45–3.93(3H, m), 4.51–4.64(1H, m), 4.99(1H, s), 6.97–7.90(19H, m), 7.66(1H, s), 7.79(2H, d, J=8.1 Hz), 7.97 (1H, t, J=4.8 Hz), 9.36–10.04(1H, br). |
| A-5 | (2-acetyl-phenyl)(2,6-difluorophenyl)methanone group | 0.81(1H, d, J=6.6 Hz), 0.91(1H, d, J=6.6 Hz) 1.52–1.83 (2H, m), 1.95–2.12(1H, m), 2.27(2H, d, J=6.8 Hz), 2.47–2.65 (2H, m), 3.53–3.90(3H, m), 4.50–4.63(1H, m), 4.95(1H, s), 6.91–7.13(7H, m), 7.17–7.43(8H, m), 7.45–7.71(4H, m) 7.75 (1H, s), 7.88(2H, d, J=8.4 Hz), 8.26(1H, t, J=5.1 Hz), 8.88–9.74(1H, br). |
| A-6 | (2-acetyl-phenyl)(2,4-difluorophenyl)methanone group | 0.84(1H, d J=6.3 Hz), 0.94(1H, d, J=6.3 Hz) 1.54–1.84 (2H, m), 1.94–2.12(1H, m), 2.35(2H, d, J=6.9 Hz), 2.64–2.81 (2H, m), 3.48–3.90(3H, m), 4.39–4.53(1H, m), 4.99(1H, s), 6.76–7.74(18H, m), 7.71(1H, s), 7.80(2H, d, J=8.4 Hz), 7.88 (1H, t, J=5.1 Hz), 8.80–9.66(1H, br). |
| A-7 | (2-acetyl-6-fluorophenyl)(2,4-difluorophenyl)methanone group | 0.75–0.95(1H, br), 0.93(1H, d, J=6.6 Hz), 1.52–1.94(2H, m), 1.98–2.18(1H, m), 2.36(2H, d, J=6.3 Hz), 2.44–2.84(2H, m), 3.50–4.00(3H, m), 4.38–4.62(1H, m), 4.97(1H, s), 6.78–8.42 (18H, m), 7.76(1H, s), 7.84(2H, d, J=8.4 Hz), 8.00–8.12(1H, br), 8.84–9.62(1H, br). |

TABLE 1-continued

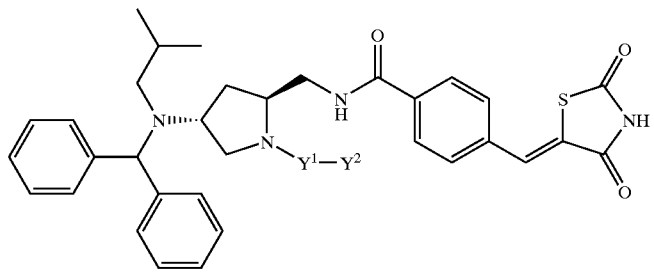

| Compound No. | —Y¹—Y² | NMR (CDCl₃) δ ppm |
|---|---|---|
| A-8 | acetyl-difluorobenzoyl-phenyl | 0.82(1H, d, J=6.6 Hz), 0.93(1H, d, J=6.6 Hz), 1.57–1.84 (2H, m), 1.92–2.12(1H, m), 2.31(2H, d, J=6.9 Hz), 2.55–2.76 (2H, m), 3.47–3.89(3H, m), 4.44–4.59(1H, m), 4.97(1H, s), 6.87–7.65(18H, m), 7.68(1H, s), 7.82(2H, d, J=8.7 Hz), 7.99 (1H, t, J=5.3 Hz), 9.22–10.0 1H, br). |
| A-9 | acetyl-difluorobenzoyl-phenyl | 0.84(1H, d, J=6.6 Hz), 0.93(1H, d, J=6.6 Hz), 1.61–1.85 (2H, m), 1.98–2.14(1H, m), 2.21–2.39(2H, m), 2.55(2H, d, J= 7.8 Hz), 3.56–3.85(3H, m), 4.45–4.57(1H, m), 4.97(1H, s), 6.90–7.41(16H, m), 7.48–7.62(2H, m), 7.72(1H, s), 7.84(2H, d, J=8.1 Hz), 8.06(1H, t, J=5.3 Hz), 9.12–9.66(1H, br). |

TABLE 2

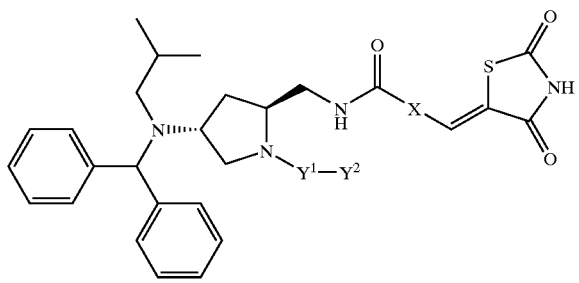

| Compound No. | X | —Y¹—Y² | NMR (CDCl₃) δ ppm |
|---|---|---|---|
| A-10 | p-phenylene | acetyl-MeO-fluorobenzoyl-fluorophenyl | 0.82(1H, d, J=6.6 Hz), 0.92(1H, d, J=6.6 Hz), 1.54–1.82(2H, m), 1.96–2.13(1H, m), 2.29(2H, d, J=7.2 Hz), 2.49–2.71(2H, m), 3.53–3.90(3H, m), 3.90(3H, s), 4.49–4.61(1H, m), 4.95(1H, s), 6.77 (1H, d, J=2.4 Hz), 6.87–7.58 (17H, m), 7.72(1H, s), 7.87(2H, d, J=8.7 Hz), 8.22(1H, t, J=5.4 Hz), 8.98–9.76(1H, br). |
| A-11 | p-phenylene | acetyl-Cl-fluorobenzoyl-fluorophenyl | 0.85(1H, d, J=6.3 Hz), 0.94(1H, d, J=6.3 Hz), 1.52–1.85(2H, m), 1.98–2.14(1H, m), 2.24–2.38(2H, m), 2.50–2.66(2H, m), 3.52–3.85 (3H, m), 4.45–4.57(1H, m), 4.98 (1H, s), 6.88–7.61(18H, m), 7.73 (1H, s), 7.85(2H, d, J=8.1 Hz), 8.04(1H, t, J=5.1 Hz), 8.60–9.90 (1H, br). |

TABLE 2-continued

| Compound No. | X | —Y¹—Y² | NMR (CDCl₃) δ ppm |
|---|---|---|---|
| A-12 | (2,5-thiophene) | (2-acetyl-phenyl)(2,4-difluorophenyl)methanone group | 0.80(3H, d, J=6.6 Hz), 0.91(3H, d, J=6.6 Hz), 1.60–1.78(2H, m), 1.95–2.10(1H, m), 2.31(2H, m), 2.69(2H, m), 3.51–3.86(3H, m), 4.49(1H, m), 4.96(1H, s), 6.88–7.38(14H, m), 7.40–7.64(5H, m), 7.83(1H, s), 8.06(1H, t, J=5.1 Hz), 9.10(1H, br. s). |

TABLE 3

| Compound No. | R¹ | R¹⁶ | n | NMR (CDCl₃) δ ppm |
|---|---|---|---|---|
| A-13 | 2-biphenylmethyl | sec-butyl (Me/Me) | 0 | 0.71(3H, d, J=6.5 Hz), 0.77(3H, d, J=6.5 Hz), 1.43–1.58(1H, m), 1.71–1.81(1H, m), 1.94–2.18(3H, m), 2.97(1H, dd, J=7.1, 11.2 Hz), 3.16(1H, dd, J= 7.7, 11.2 Hz), 3.37–3.51(1H, m), 3.45(2H, s), 3.53–3.64(1H, m), 3.71–3.81(1H, m), 4.55–4.65(1H, m), 6.85–7.01(2H, m), 7.10–7.43(11H, m), 7.44–7.64(5H, m), 7.73(1H, s), 7.91(1H, d, J= 8.4 Hz), 8.23(1H, t, J=5.0 Hz). |
| A-14 | 2-biphenylmethyl | sec-butyl (Me/Me) | 1 | 0.72(3H, d, J=6.5 Hz), 0.78(3H, d, J=6.5 Hz), 1.45–1.58(1H, m), 1.67–1.76(1H, m), 1.93–2.18(3H, m), 2.98(1H, dd, J=6.7, 11.0 Hz), 3.15(1H, dd, J=7.7, 11.0 Hz), 3.35–3.62(2H, m), 3.45(2H, s), 3.62–3.72(1H, m), 4.47–4.58(1H, m), 6.51(1H, d, J=15.7 Hz), 6.84–7.01(2H, m), 7.10–7.70(2H, m), 7.71(1H, s). |
| A-15 | CH(i-Bu)(i-Bu) | sec-butyl (Me/Me) | 0 | 0.57–1.64(25H, m), 1.81–2.33(4H, m), 2.68 (1H, quint, J=6.6 Hz), 2.92–3.08(1H, m), 3.20–3.33(1H, m), 3.56–3.93(3H, m), 4.61–4.74(1H, m), 6.85–7.04(2H, m), 7.38–8.42 (11H, m). |
| A-16 | diphenylmethyl (CH(Ph)₂) | benzyl (CH₂Ph) | 0 | 1.74–1.89(1H, m), 2.05–2.21(1H, m), 2.90 (1H, dd, J=7.8, 11.4 Hz), 3.06(1H, dd, J= 7.8, 11.4 Hz), 3.50–4.01(5H, m), 4.51–4.63 (1H, m), 4.82(1H, s), 6.84–7.64(24H, m), 7.71(1H, s), 7.86(2H, d, J=8.1 Hz), 8.15 (1H, t, J=4.8 Hz), 9.02–10.0(1H, br). |

TABLE 3-continued
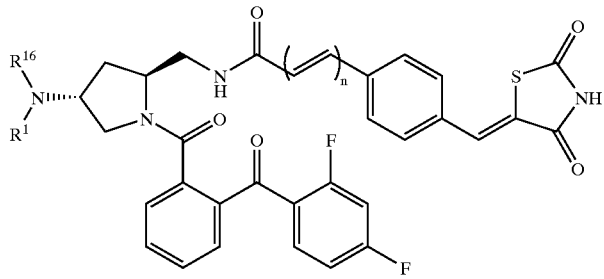
| Compound No. | R¹ | R¹⁶ | n | NMR (CDCl₃) δ ppm |
|---|---|---|---|---|
| A-17 | (diphenylmethyl with CH₃) | (phenylethyl) | 1 | 1.66–1.84(1H, m), 2.03–2.19(1H, m), 2.92 (1H, dd, J=7.2, 11.2 Hz), 3.12(1H, dd, J= 7.8, 11.2 Hz), 3.40–4.01(5H, m), 4.45–4.57 (1H, m), 4.84(1H, s), 6.45(1H, d, J=15.9 Hz), 6.81–7.68(28H, m), 7.70(1H, s), 9.20– 10.0(1H, br). |
Example 18
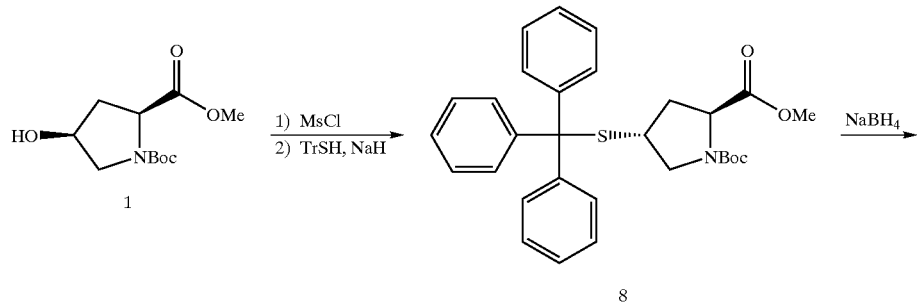
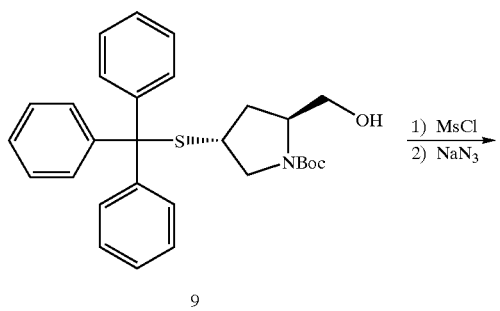
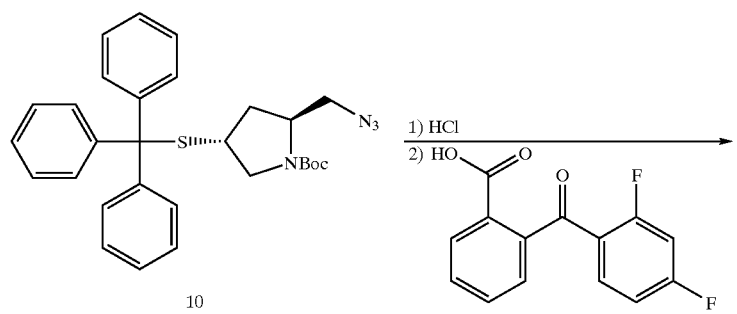

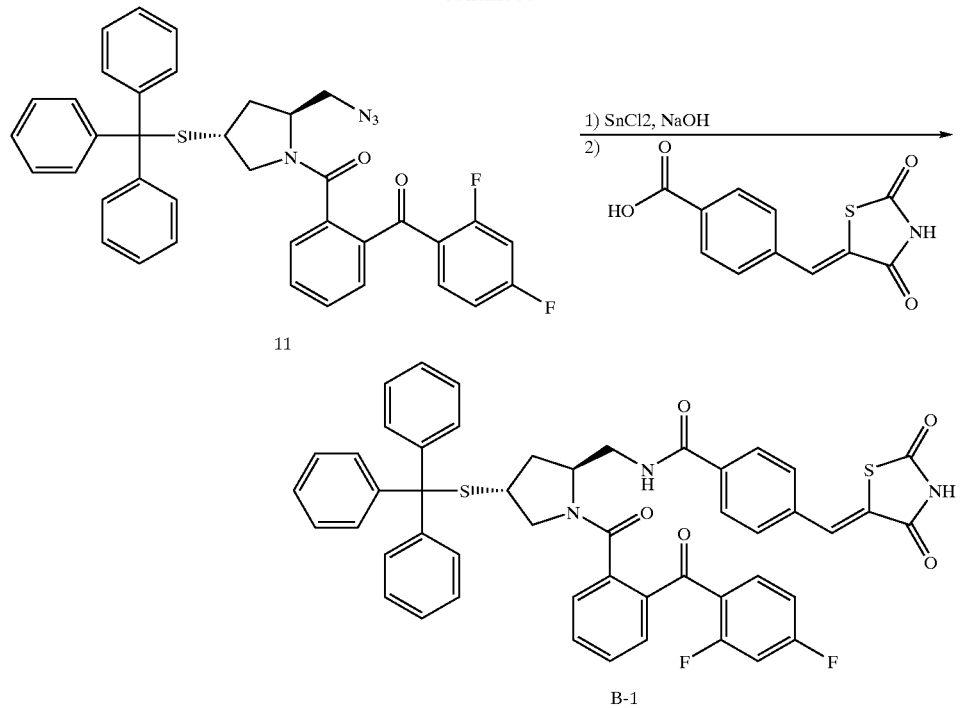

(1) 1→8

To a solution of alcohol (1) 1.15 g (4.69 mmol) in toluene (10 mL) were added triethylamine (0.4 mL) and methanesulfonyl chloride (0.4 mL) in an ice bath. After the reaction mixture was stirred at same temperature for 20 min, it was poured into water, and the resulting mixture was extracted with ethyl acetate twice. The organic layer was washed with 5% aqueous sodium hydrogen carbonate solution, brine and dried over sodium magnesium. Evaporation of the solvent under reduced pressure gave the 4-position OMs form.

After 60% sodium hydride 193 mg (4.83 mmol) was washed with n-hexane, to a suspension of it in THF (3 mL) was added a solution of trimethylmercaptan (1.335 g, 4.83 mmol) in THF (4 mL) in an ice bath and then the mixture was stirred for 25 min. After to the mixture was added a solution of the above-mentioned 4 position-OMs form in THF (4 mL), the reaction mixture was stirred at room temperature for 2 h. The reaction mixture was poured into water and the resulting mixture was extracted with ethyl acetate twice, and then the organic layer was washed 0.8N hydrochloric acid, 0.7N aqueous sodium carbonate solution, brine and dried over magnesium sulfate. After evaporation of the solvent under reduced pressure, the residue was crystallized from ethyl acetate-n-hexane to obtain the product (8) (1.27 g, 53.8%).

$^1$H-NMR (CDCl$_3$) ™(ppm): 1.35–1.42 (9H, m), 1.75–1.90 (1H, m), 2.82–3.35 (3H, m), 3.57–3.62 (4H, m), 4.08–4.217 (1H, m), 7.18–7.31 (9H, m), 7.42–7.45 (6H, m), m/Z 504 (C$_{30}$H$_{33}$NO$_4$S: M/Z 504).

(2) 8→9→10

According to the preparation of the alcohol (5) in example 1, the alcohol (9) was obtained from the above-mentioned compound (8) as a starting material. The azide (10) was obtained in a manner similar to that described in the synthesis of the alcohol (6) in example 1 using the alcohol (9) which was obtained without purification.

$^1$H-NMR (CDCl$_3$) δ (ppm): 1.42 (9H, s), 1.50–1.64 (1H, m), 1.71–1.81 (1H, m), 2.72–3.39 (5H, m), 3.70–3.89 (1H, m), 7.20–7.32–7.31 (9H, m), 7.46 (6H, d, J=7.8 Hz).

IR (CHCl$_3$) ν$_{max}$(cm$^{-1}$): 2105, 1686.

Elemental analysis (C$_{29}$H$_{32}$N$_4$O$_2$S) Calcd.: C, 69.57; H, 6.44; N, 11.19; S, 6.40%. Found: C, 69.30; H, 6.56; N, 11.23; S, 6.31%.

(3) 10→11

According to the preparation of the compound (7) in example 1, the compound (11) was yielded from the above-mentioned compound (10) as a starting material.

$^1$H-NMR (CDCl$_3$) δ (ppm): 1.88–1.97(2H, m), 2.58 (1H, dd, J=7.2, 10.8 Hz), 2.69 (1H, dd, J=7.2, 10.8 Hz), 3.07 (1H, quintet, J=7.5 Hz), 3.35 (1H, dd, J=3.3, 6.3 Hz), 3.49 (1H, dd, J=5.7, 12.3 Hz), 4.20–4.25 (1H, m), 6.80–7.00 (2H, m), 7.15–7.64 (20H, m).

IR (CHCl$_3$) ν$_{max}$(cm$^{-1}$): 2103, 1669, 1640, 1609.

Elemental analysis(C$_{38}$H$_{30}$N$_4$O$_2$SF$_2$) Calcd. C, 71.63; H, 4.86; N, 8.33; S, 4.77; F, 5.65%. Found C, 71.80; H, 4.99; N, 8.29; S, 4.81; F, 5.52%.

(4) 11→B-1

The compound (B-1) was obtained in a manner similar to that described in the synthesis of the compound (A-1) in Example 1 using the above-mentioned compound (11) as a starting material.

$^1$H-NMR (CDCl$_3$) δ(ppm): 2.03–2.21 (2H, m), 2.26–2.34 (1H, m), 2.51 (1H, dd, J=7.8, 1.1.1 Hz), 2.90–3.01 (1H, m), 3.77–3.93 (2H, m), 4.19–4.46 (1H, m), 6.93–7.10 (10H, m), 7.22–7.29 (7H, m), 7.39 (2H, d, J=8.1 Hz), 7.51–7.65 (4H, m), 7.79 (1H, s), 7.88 (2H, d, J=8.1 Hz), 8.12–8.16 (1H, m), 9.35–9.50 (1H, br. s).

mp.: 158–160° C.

IR(KBr) μ$_{max}$(cm$^{-1}$): 3411, 1751, 1709, 1662, 1610, 1537, 1498, 1284.

Elemental analysis (C$_{49}$H$_{37}$N$_3$O$_5$S$_2$F$_2$.0.65EtOH.H$_2$O とUて) Calcd.: C, 67.28; H, 4.59; N, 4.68; S, 7.14; F, 4.23%. Found: C, 67.48; H, 4.61; N, 4.86; S, 7.10; F, 4.13%.

[a]$_D^{23}$: −190.4±2.3° (c, 1.002, CHCl$_3$)

The compounds (B-2) to (B-25) were synthesized in a manner similar to that described in the above method. The results were shown in Tables 4 to 9.

TABLE 4
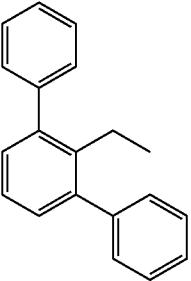
| Compound No. | R¹ | NMR (CDCl₃) δ ppm |
|---|---|---|
| B-2 | 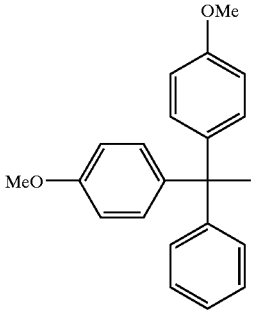 | 1.54–1.85(2H, m), 2.67–2.85(2H, m), 3.13(1H, dd, J=5.7, 11.4 Hz), 3.40–3.55(1H, m), 3.49 and 3.58(2H, ABq, $J_{AB}$=11.7 Hz), 3.74–3.86(1H, m), 4.30–4.43(1H, m), 6.81–6.99(2H, m), 7.15–7.61 (20H, m), 7.76(1H, s), 7.96(2H, d, J=8.4 Hz), 8.25(1H, t, J=5.0 Hz). |
| B-3 | 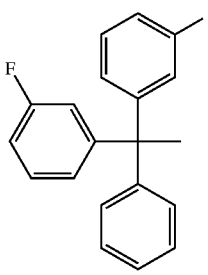 | 2.11–2.29(3H, m), 2.58(1H, dd, J=7.5 11.1 Hz), 2.97(1H, m), 3.71(6H, s), 3.73–3.95(2H, m), 4.40–4.45(1H, m), 6.60–6.63(3H, m), 6.91–7.08 (3H, m), 7.06–7.15(7H, m), 7.21–7.30(2H, m), 7.41(2H, d, J=8.7 Hz), 7.50–7.66(4H, m), 7.80 (1H, s), 7.91(2H, d, J=8.7 Hz), 8.12–8.15(1H, m), 9.03(1H, br. s). |
| B-4 | | 2.07–2.23(2H, m), 2.30–2.42(1H, m), 2.55(1H, dd, J=8.1, 11.1 Hz), 2.90–3.05(1H, m), 3.85–3.98 (2H, m), 4.37–4.47(1H, m), 6.63–6.77(2H, m), 6.89–7.69(20H, m), 7.81(1H, s), 7.93(2H, d, J= 8.7 Hz), 8.11(1H, t, J=5.6 Hz), 8.90–9.15(1H, br). |

TABLE 5

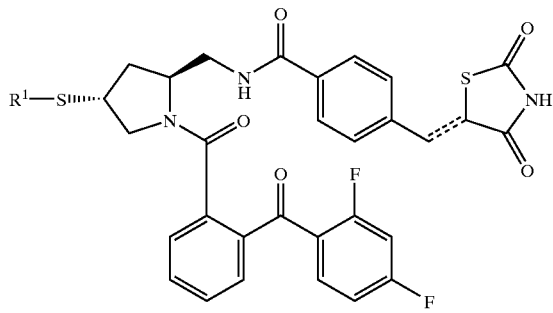

| Compound No. | R¹ | NMR (CDCl₃) δ ppm |
|---|---|---|
| B-5 | 3,5-difluorophenyl-diphenyl-methyl (F-C₆H₃(F)-C(Ph)₂-) | 2.06–2.23(2H, m), 2.29–2.40(1H, m), 2.54(1H, dd, J=8.1, 11.0 Hz), 2.89–3.04(1H, m), 3.84–3.98(2H, m), 4.37–4.47(1H, m), 6.45(1H, tt, J=2.1, 8.4 Hz), 6.77–7.69(21H, m), 7.81(1H, s), 7.93(2H, d, J=8.4 Hz), 8.11(1H, t, J=5.6 Hz), 8.58–9.20(1H, br). |
| B-6 | 3,5-dimethylphenyl-diphenyl-methyl (Me-C₆H₃(Me)-C(Ph)₂-) | 2.06–2.23(3H, m), 2.11(6H, s), 2.27–2.34(1H, m), 2.55(1H, dd, J=8.1, 11.1 Hz), 2.91–3.02 (1H, m), 3.73–3.92(2H, m), 4.40–4.43(1H, m), 6.62(1H, s), 6.89(2H, s), 6.94–7.12(8H, m), 7.21–7.28(6H, m), 7.38(2H, d, J=8.7 Hz), 7.51–7.65(4H, m), 7.78(1H, s), 7.86(2H, d, J=8.7 Hz), 8.11–8.15(1H, m), 9.78(1H, br. s). |
| B-7 | bis(3-methylphenyl)-phenyl-methyl | 2.03–2.10(1H, m), 2.13(3H, m), 2.15(3H, m), 2.28–2.35(1H, m), 2.55(1H, dd, J=8.4, 11.1 Hz), 2.90–3.01(1H, m), 3.74–3.92(2H, m), 4.38–4.45(1H, m), 6.77–6.82(2H, m), 6.91–7.14 (10H, m), 7.25(3H, t, J=7.2 Hz), 7.39(2H, d, J=8.4 Hz), 7.51–7.64(4H, m), 7.79(1H, s), 7.86 (2H, d, J=8.7 Hz), 8.10–8.14(1H, m), 9.20(1H, s). |
| B-8 | triphenylmethyl (trityl) | 1.98(1H, m), 2.15(1H, m), 2.25–2.40(1H, m), 2.47(1H, m), 2.94(1H, m), 3.10(1H, dd, J=9.9, 14.1 Hz), 3.53(1H, dd, J=3.6, 14.1 Hz), 3.84(2H, m), 4.38(1H, m), 4.46(1H, dd, J=3.6, 9.9 Hz), 6.90–7.30(20H, m), 7.46–7.65,(4H, m), 7.56(2H, dd, J=6.3, 8.1 Hz), 8.02(1H, m), 8.90–9.20(1H, m). |

TABLE 6

[Structure: R¹-S-pyrrolidine with substituents including 2,4-difluorobenzoyl, benzoyl, amide linker to cinnamide, phenyl, thiazolidine-2,4-dione]

| Compound No. | R¹ | NMR (CDCl₃) δ ppm |
|---|---|---|
| B-9 | trityl (triphenylmethyl) group | 2.10–2.20(2H, m), 2.27(1H, dd, J=7.2, 7.5 Hz), 2.52 (1H, dd, J=7.2, 7.4 Hz), 2.92–3.05(1H, m), 3.61–3.71 (1H, m), 3.74–3.83(1H, m), 4.36(1H, m), 6.48(1H, d, J=15.6 Hz), 6.90–7.70(28H, m), 7.77(1H, s), 9.40 (1H, br. s). |
| B-10 | 2,6-diphenylphenyl-ethyl group | 1.55–1.83(2H, m), 2.67–2.85(2H, m), 3.13(1H, dd, J= 5.6, 11.3 Hz), 3.36–3.79(2H, m), 3.50 and 3.58(2H, ABq, J_AB=11.7 Hz), 4.21–4.33(1H, m), 6.56(1H, d, J=15.9 Hz), 6.82–7.01(2H, m), 7.16–7.68(24H, m), 7.74(1H, s). |
| B-11 | (4-methoxyphenyl)diphenylmethyl group | 2.14–2.19(2H, m), 2.34(1H, dd, J=6.9, 11.1 Hz), 2.55(1H, dd, J=6.9 11.1 Hz), 2.98(1H, quint, J= 7.0 Hz), 3.61–3.76(2H, m), 3.72(3H, s), 4.36(1H, m), 6.48(1H, d, J=15.6 Hz), 6.65–6.69(2H, m), 6.81–7.35(23H, m), 7.77(1H, s). |
| B-12 | bis(4-methoxyphenyl)phenylmethyl group | 2.17(2H, t, J=6.9 Hz), 2.42(1H, dd, J=6.9, 11.1 Hz), 2.59(1H, dd, J=6.9, 11.1 Hz), 2.98(1H, quint, J=7.5 Hz), 3.62–3.76(2H, m), 3.73(6H, s), 4.37 (1H, m), 6.50(1H, d, J=15.3 Hz), 6.65–6.69(3H, m), 6.78–7.34(22H, m), 7.76(1H, s). |

TABLE 7
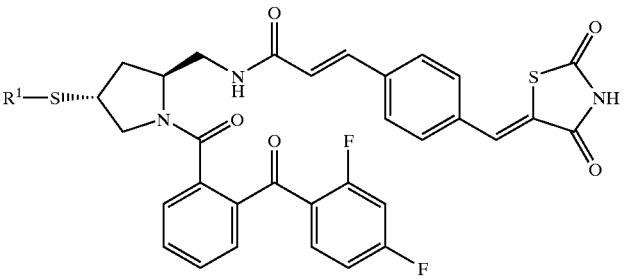
| Compound No. | R¹ | NMR (CDCl₃) δ ppm |
|---|---|---|
| B-13 | 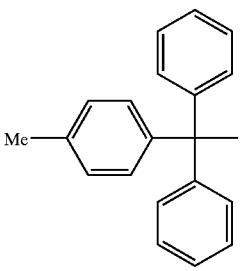 | 2.15(1H, t, J=6.6 Hz), 2.22(3H, s), 2.52(1H, dd, J=6.6, 11.1 Hz), 2.99(1H, quint, J=3.9 Hz), 3.59–3.67(1H, m), 3.77(1H, td, J=3.9, 14.5 Hz), 4.37(1H, m), 6.48(1H, d, J=15.9 Hz), 6.89–7.68 (26H, m), 7.76(1H, s). |
| B-14 | 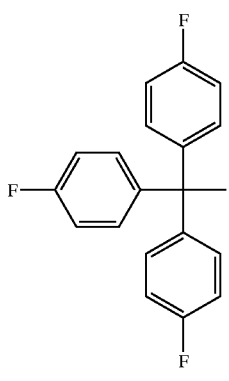 | 2.04–2.25(2H, m), 2.35–2.55(2H, m), 2.88–3.04 (1H, m), 3.84(2H, dd, J=3.5, 5.6 Hz), 4.27–4.38 (1H, m), 6.51(1H, d, J=15.9 Hz), 6.75–6.87(5H, m), 6.93–7.04(2H, m), 7.14–7.68(17H, m), 7.38 (1H, d, J=15.9 Hz), 7.81(1H, s). |
| B-15 | 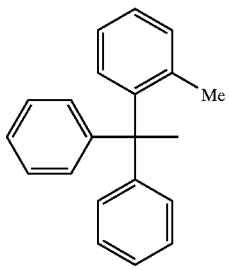 | 1.75,(3H, s), 2.11–2.21(3H, m), 2.53(1H, dd, J= 7.2, 11.1 Hz), 2.96(1H, quint, J=7.5 Hz), 3.60– 3.69(1H, m), 3.76(1H, td, J=3.9, 14.5 Hz), 4.37 (1H, m), 6.46(1H, d, J=15.9 Hz), 6.81–7.68(26H, m), 7.76(1H, s), 9.49–9.61(1H, m). |
| B-16 | 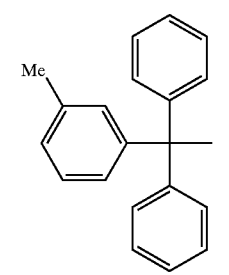 | 2.16(3H, s), 2.13–2.28(3H, m), 2.54(1H, dd, J= 7.5, 11.1 Hz), 2.98(1H, quint, J=7.5 Hz), 3.62– 3.71(1H, m), 3.77(1H, td, J=6.9, 13.8 Hz), 4.32–4.90(1H, m), 6.47(1H, d, J=15.9 Hz), 6.85– 7.66(26H, m), 7.77(1H, s), 9.48(1H, br. s). |

TABLE 8
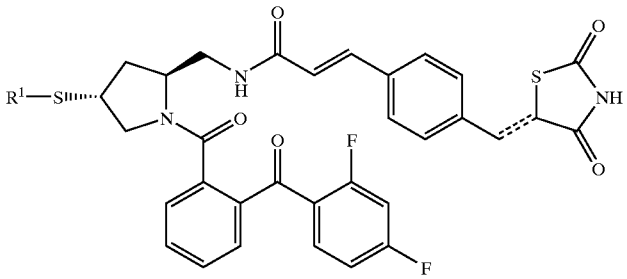
| Compound No. | R¹ | NMR (CDCl₃) δ ppm |
|---|---|---|
| B-17 | 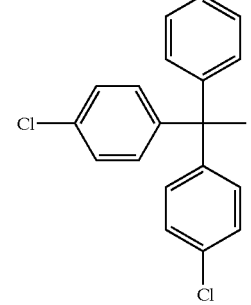 | 2.17–2.26(2H, m), 2.41–2.54(2H, m), 2.92–3.03 (1H, m), 3.83–3.87(2H, m), 4.31–4.35(1H, m), 6.51(1H, d, J=16.2 Hz), 6.95–7.66(24H, m), 7.81 (1H, s). |
| B-18 | 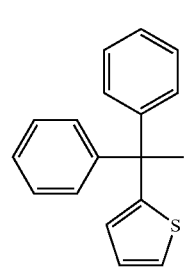 | 1.08(6H, s), 2.13(2H, t, J=6.9 Hz), 2.37(1H, dd, J=6.9, 11.1 Hz), 2.57(1H, dd, J=6.9, 11.1 Hz), 2.71(1H, quint, J=6.9 Hz), 3.56–3.65(1H, m), 3.76(1H, td, J=6.9, 13.8 Hz), 4.34–4.42(1H, m), 6.48(1H, d, J=15.6 Hz), 6.88–7.65(26H, m), 9.68 (1H, br. s). |
| B-19 | 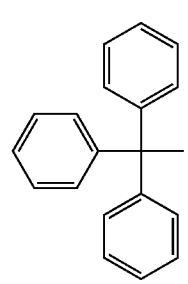 | 2.10–2.35(2H, m), 3.33(1H, dd, J=2.7, 11.4 Hz), 3.42–3.72(2H, m), 3.94(1H, m), 4.54(1H, m), 5.54(1H, dd, J=0.9, 3.6 Hz), 5.55(1H, s), 6.55 (1H, d, J=16.2 Hz), 6.86–7.00(3H, m), 7.16(4H, d, J=7.2 Hs), 7.21–7.67(20H, m), 7.79(1H, s), 8.80(1H, s). |
| B-20 | — | 2.10–2.31(2H, m), 2.48(1H, dd, J=6.9, 11.1 Hz), 2.98(1H, m), 3.10(1H, m), 3.51(1H, m), 3.63–3.83(2H, m), 4.32(1H, m), 4.69(1H, dd, J=6.9, 9.9 Hz), 6.35(1H, d, J=15.9 Hz), 6.84–7.67(27H, m), 9.66(1H, br. s). |

TABLE 9

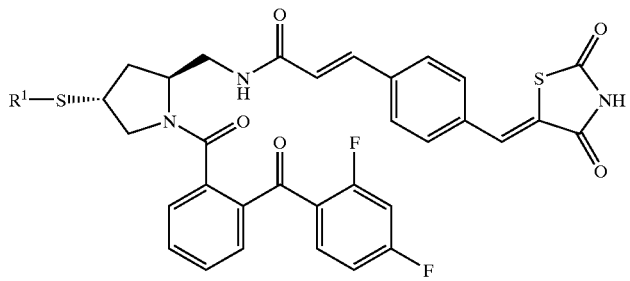

| Compound No. | R¹ | NMR (CDCl₃) δ ppm |
|---|---|---|
| B-21 | 3,3'-di(m-tolyl)phenylmethyl group with Me | Me 2.15(3H, s), 2.16(3H, s), 2.15–2.31(3H, m), 2.56 (1H, dd, J=7.5, 11.1 Hz), 2.93–3.03(1H, m), 3.63–3.81(2H, m), 4.33–4.37(1H, m), 6.47(1H, d, J=15.6 Hs), 6.83–7.64(24H, m), 7.77(1H, s), 9.60 (1H, br. s). |
| B-22 | 3,5-dimethylphenyl diphenyl methyl | Me 2.14(6H, s), 2.14–2.29(3H, m), 2.56(1H, dd, J= 7.2, 11.1 Hz), 2.97(1H, quint, J=7.2 Hz), 3.62– 3.70(1H, m), 3.77(1H, td, J=3.9, 13.2 Hz), 4.32– 4.37(1H, m), 6.47(1H, d, J=15.9 Hz), 6.69(1H, s), 6.89–7.15(10H, m), 7.26–7.65(14H, m), 7.76 (1H, s), 9.69(1H, br. s). |
| B-23 | 2-fluorophenyl diphenyl methyl | 2.08–2.26(3H, m), 2.49(1H, dd, J=7.2, 11.1 Hz), 2.91(1H, quint, J=7.5 Hz), 3.60–3.84(2H, m), 4.27–4.40(1H, m), 6.47(1H, d, J=15.6 Hz), 6.69– 6.79(1H, m), 6.85–7.05(5H, m), 7.09–7.83(21H, m), 7.78(1H, s). |
| B-24 | 3-fluorophenyl diphenyl methyl | 2.07–2.33(3H, m), 2.53(1H, dd, J=7.2, 11.4 Hz), 2.99(1H, quint, J=7.5 Hz), 3.63–3.86(2H, m), 4.30–4.41(1H, m), 6.48(1H, d, J=15.9 Hz), 6.69– 6.79(1H, m), 6.88–7.69(26H, m), 7.78(1H, s). |

TABLE 9-continued

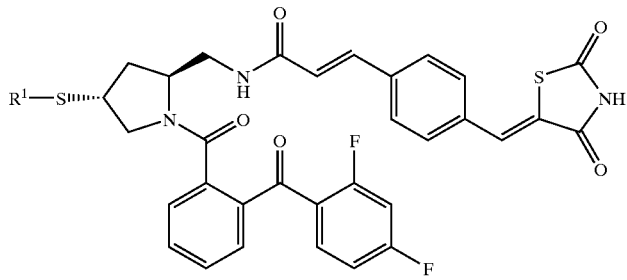

| Compound No. | R[1] | NMR (CDCl₃) δ ppm |
|---|---|---|
| B-25 | <image structure: F-C₆H₄-C(Ph)(Ph)-> | 2.08–2.33(3H, m), 2.50(1H, dd, J=7.2, 11.1 Hz), 2.90–3.05(1H, m), 3.65–3.87(2H, m), 4.29–4.40 (1H, m), 6.49(1H, d, J=15.9 Hz), 6.74–6.84(2H, m), 6.89–7.68(25H, m), 7.78(1H, s). |

Example 43 to 45

Furthermore, the compound (C-1) was obtained in a manner similar to that described in the method A-2 of WO/983397, the compound (C-2) was obtained in a manner similar to that described in the method A-3, and the compound (C-3) was obtained in a manner similar to that described in the method B-1. The structures and NMR data were shown below.

Compound (C-1)

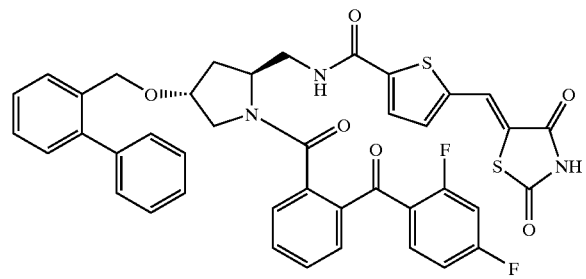

¹H-NMR (CDCl₃) δ (ppm): 1.88 (1H, m), 2.24 (1H, m), 3.21 (1H, dd$_{AB}$, J=3.9, 11.7 Hz), 3.31 (1H, d$_{AB}$, J=11.7 Hz), 3.65 (1H, td, J=5.7, 14.1 Hz), 3.92 (1H, m), 4.00 (1H, m), 4.23(1H, d$_{AB}$, J=11.3 Hz), 4.36 (1H, d$_{AB}$, J=11.3 Hz), 4.51 (1H, m), 6.85–7.02 (2H, m), 7.18–7.69 (15H, m), 7.89 (1H, s), 8.24 (1H, t, J=5.1 Hz), 8.74 (1H, br. s).

Compound (C-2)

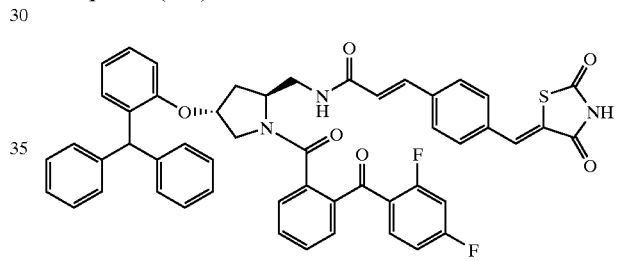

¹H-NMR δ: 1.94–2.07 (1H, m), 2.15–2.32 (1H, m), 3.37 (2H, s), 3.57–3.71 (1H, m), 3.88–4.10 (2H, m), 4.72 (1H, br. s), 5.81. (1H, s), 6.61–7.76 (28H, m), 7.78 (1H, s), 8.90–10.2 (1H, br).

Compound (C-3)

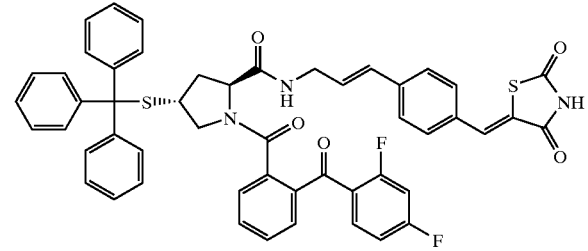

¹H-NMR (CDCl₃) δ: 2.14 (1H, ddd, J=8.7, 10.4, 13.2 Hz), 2.38 (1H, dd, J=7.2, 10.8 Hz), 2.55 (1H, ddd, J=2.4, 6.5, 13.2 Hz), 2.65 (1H, dd, J=8.4, 10.8 Hz), 2.99–3.15 (1H, m), 3.92–4.12 (2H, m), 4.72 (1H, dd, J=2.4, 8.7 Hz), 6.19 (1H, dt, J=15.9, 5.6 Hz), 6.41 (1H, d, J=15.9 Hz), 6.76–6.93 (2H, m), 7.02–7.70 (25H, m), 8.94–11.2 (1H, br).

Test Example 1 cPLA$_2$ Inhibitory Activity

The compounds of the present invention were tested for the cPLA$_2$ inhibitory activity according to the method disclosed in R. M. Kramer, E. F. Roberts, J. Manetta, and J. E. Putnam, J. Biol. Chem., 1991, 266, 5268–5272 as outlined below.

Using the 1-palmitoyl-2-[$^{14}$C]-arachidonoyl-sn-glycero-3-phosphocholine as a substrate, liposomes (a substrate solution) containing the substrate of which concentration was 2.5 $\mu$M in the reaction mixture and sn-1,2-dioleoylglycerol of which concentration was 1.25 $\mu$M in the reaction mixture at the molar ratio of 2:1 were prepared. The reaction mixture includes 50 mM HEPES buffer (pH 7.5), 1 mM calcium chloride, 150 mM sodium chloride, 0.1 mg/ml bovine serum albumin, and 1.7 mM dithiothreitol. To the reaction mixture was added the compound of the present invention and the substrate solution. The reaction was allowed to start by adding an enzyme and continued for 15 min at 37° C. The fatty acids released by the reaction were extracted by the method described in V. P. Dole, and H. Meinertz, J. Biol. Chem., 1960, 235, 2595–2599 and its radiation activity was measured on a liquid scintillation counter. Control was obtained by conducting the experiment in the same manner except that a compound of the present invention was not added. The results were shown in Tables 10.

TABLE 10

| Compound No. | IC$_{50}$($\mu$M) | Compound No. | IC$_{50}$($\mu$M) |
|---|---|---|---|
| A-1 | 0.033 | B-7 | 0.0014 |
| A-2 | 0.014 | B-8 | 0.0012 |
| A-3 | 0.094 | B-9 | 0.00060 |
| A-5 | 0.0074 | B-10 | 0.0056 |
| A-6 | 0.0045 | B-11 | 0.0012 |
| A-7 | 0.0051 | B-12 | 0.0020 |
| A-8 | 0.0050 | B-13 | 0.0020 |
| A-9 | 0.0020 | B-14 | 0.0012 |
| A-10 | 0.029 | B-15 | 0.0012 |
| A-11 | 0.0052 | B-16 | 0.0010 |
| A-12 | 0.0021 | B-17 | 0.00063 |
| A-13 | 0.0062 | B-18 | 0.00026 |
| A-14 | 0.0018 | B-19 | 0.0029 |
| A-15 | 0.0067 | B-20 | 0.0014 |
| A-16 | 0.014 | B-21 | 0.00027 |
| A-17 | 0.0037 | B-22 | 0.00037 |
| B-1 | 0.0037 | B-23 | 0.00052 |
| B-2 | 0.020 | B-24 | 0.00036 |
| B-3 | 0.0090 | B-25 | 0.00043 |
| B-4 | 0.0026 | C-1 | 0.024 |
| B-5 | 0.0027 | C-2 | 0.0038 |
| B-6 | 0.0013 | C-3 | 0.0054 |

Test Example 2

Wistar male rats (weight 250–350 g) were used. The compound (C-4) (the compound M-17 described in WO98/33797) and the compound (B-1) shown below were dissolved in solvent containing DMSO:ethanol:polyethylene glycol 300:1% aqueous sodium hydrogen carbonate solution=10:10:30:50 (volume ratio). Anesthesia was induced with intraperitoneal injection of 40 mg/kg of pentobarbital sodium. A catheter for the administration of drugs was placed in the jugular vein. Electrocardiogram (ECG) was recorded from lead II during cardiac ischemia and 10 min reperfusion. Drugs were administrated intravenously in bolus at 30 min before reperfusion followed by 40 min infusion. Solvent containing DMSO:ethanol:polyethylene glycol 300:1% aqueous sodium hydrogen carbonate solution=10:10:30:50 (volume ratio) was administrated as vehicle in a administration experiment. A thoracotomy was performed under artificial ventilation. Left coronary artery was ligated with silicon tube for 3 min. Reperfusion was performed by cutting snare. Total duration of ventricular tachycardia (VT) and ventricular fibrillation (VF) during 10 min reperfusion were evaluated.

The result of the compound (C-4) was shown in table 11 and the result of the compound (B-1) was shown in table 12. Data are expressed as mean±S.D. Statistical analysis was performed with Welch's t-test. A value of P<0.05 was considered significant.

Compound (C-4)

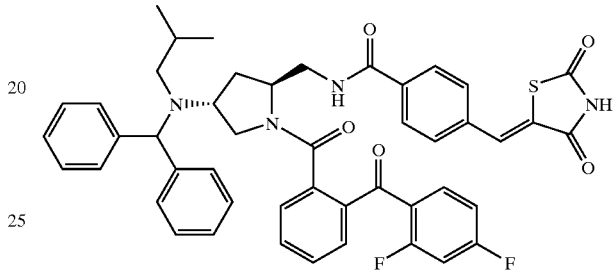

TABLE 11

| Bolus (i.v.) + Infusion (i.v.) | ventricular tachycardia (sec) | ventricular fibrillation (sec) | n |
|---|---|---|---|
| Vehicle | 54.2 ± 51.5 | 45.5 ± 106.3 | 16 |
| Compound (C-4) 0.001 mg/kg + 0.001 mg/kg/hr | 28.7 ± 50.3 | 15.1 ± 41.2 | 9 |
| 0.01 mg/kg + 0.01 mg/kg/hr | 7.6 ± 9.4# | 1.6 ± 2.9 | 12 |
| 0.1 mg/kg + 0.1 mg/kg/hr | 5.1 ± 9.3# | 0.2 ± 0.4 | 8 |

; P < 0.05 vs Vehicle

TABLE 12

| Bolus (i.v.) + Infusion (i.v.) | ventricular tachycardia (sec) | ventricular fibrillation (sec) | n |
|---|---|---|---|
| Vehicle | 84.2 ± 109.9 | 133.3 ± 196.2 | 10 |
| Compound (B-1) 0.001 mg/kg + 0.001 mg/kg/hr | 54.8 ± 100.9 | 44.5 ± 133.3 | 9 |
| 0.01 mg/kg + 0.01 mg/kg/hr | 31.1 ± 62.3* | 56.5 ± 169.5 | 9 |
| 0.1 mg/kg + 0.1 mg/kg/hr | 0.4 ± 0.9* | 0.0 ± 0.0 | 8 |

*; P < 0.01 vs Vehicle

As shown in Table 11 and 12, both the compound (C-4) and the compound (B-1) significantly reduced ventricular tachycardia induced by ischemia-reperfusion.

Formulation Example

It is to be noted that the following Formulation Examples 1 to 9 are mere illustration, but not intended to limit the scope of the invention. The term "active ingredient" means the compounds represented by the formula (1), the prodrugs thereof, their pharmaceutical acceptable salts, or their solvates.

Formulation Example 1

Hard gelatin capsules are prepared using of the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, starch, cellulose, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |

-continued

| | |
|---|---|
| Benzoic acid solution | 0.10 ml |
| Flavor | q. v. |
| Color | q. v. |
| Purified water to total | 5 ml |

The active ingredient is passed through a No. 46 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| | |
|---|---|
| Active ingredient | 127 mg |
| Trisodium citrate dihydrate | 36 mg |
| Mannitol | 180 mg |

The above materials are dissolved in water for injection such that the concentration of active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

INDUSTRIAL APPLICABILITY

The composition having cPLA$_2$ inhibiting activity was found to be useful for treating or preventing arrhythmia.

What is claimed is:

1. A method for treating arrhythmia of a mammal which comprises administration to said mammal in a pharmaceutically effective amount of a compound represented by the formula:

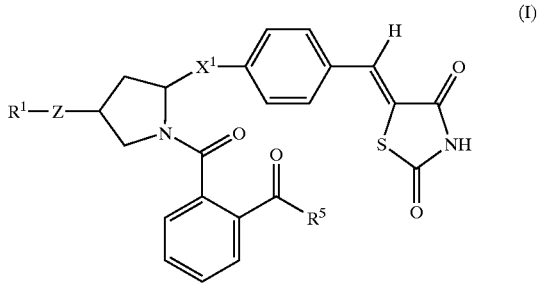

(I)

wherein $R^1$ is an optionally substituted aralkyl,

Z is —S— or —N($R^{16}$)—, wherein $R^{16}$ is a hydrogen atom or a lower alkyl;

$X^1$ is —(CH$_2$)s-N($R^{18}$)—CO—, wherein $R^{18}$ is a hydrogen atom or a lower alkyl, s is an integer from 0 to 3 or —CH$_2$N($R^{19}$)COCHCH═CH—, wherein $R^{19}$ is a hydrogen atom or a lower alkyl;

$R^5$ is an optionally substituted aryl, its prodrug, its pharmaceutically acceptable salt, or hydrate thereof.

2. A method of claim 1 for treating arrhythmia, wherein the arrhythmia occurs after ischemia reperfusion.

3. A method for treating arrhythmia of a mammal which comprises administration to said mammal in a pharmaceutically effective amount of a compound selected from the group of compounds represented by the formulae:

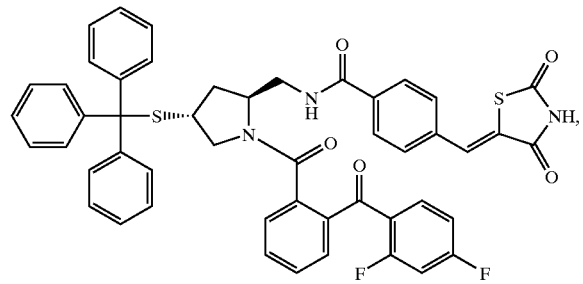

B-1

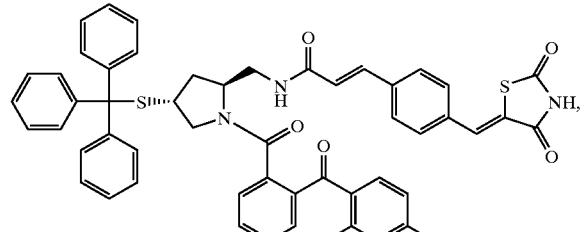

B-9

-continued

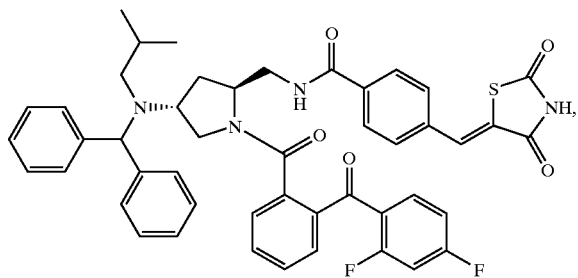
C-4 and

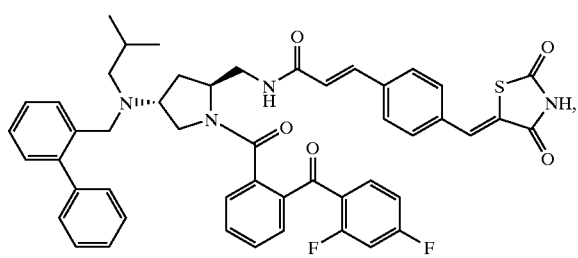
A-14 its prodrug, its pharmaceutically acceptable salt, or hydrate thereof.

4. A method of claim 3 for treating arrhythmia, wherein the arrhythmia occurs after ischemia reperfusion.

5. A compound selected from the group of compounds represented by the formulae:

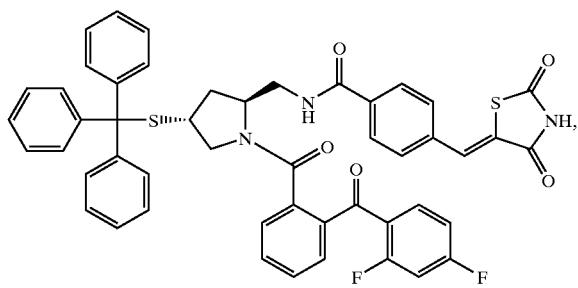
B-1

-continued

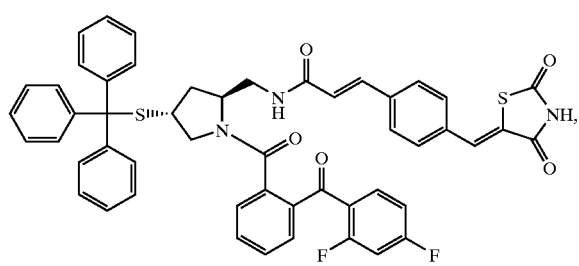
B-9 its prodrug, its pharmaceutically acceptable sail, or hydrate thereof.

6. A pharmaceutical composition, comprising, in an acceptable medium for pharmaceutical compositions, at least one compound selected from the group of compounds represented by the formulae:

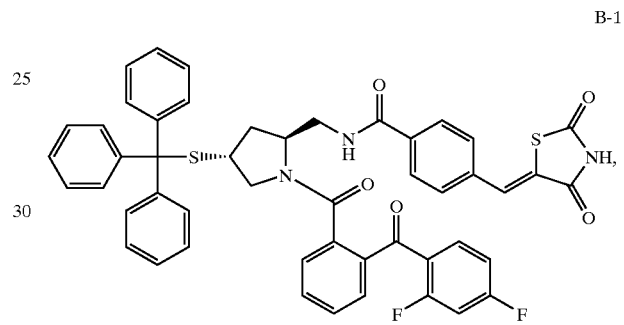
B-1

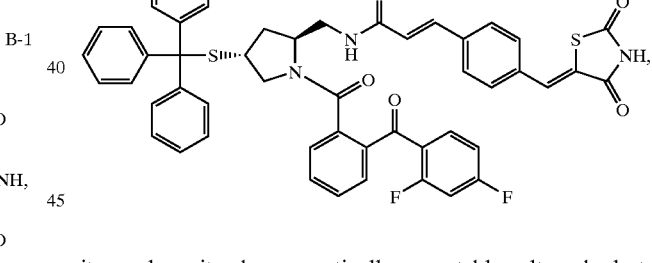
B-9 its prodrug, its pharmaceutically acceptable salt, or hydrate thereof.

* * * * *